US012144896B2

(12) United States Patent
Lollo et al.

(10) Patent No.: US 12,144,896 B2
(45) Date of Patent: Nov. 19, 2024

(54) DRUG DELIVERY SYSTEM

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE - CNRS -, Paris (FR); UNIVERSITE D'ANGERS, Angers (FR); CENTRE HOSPITALIER UNIVERSITAIRE D'ANGERS, Angers (FR)

(72) Inventors: Giovanna Lollo, Lyons (FR); Jean-Pierre Benoit, Angers (FR); Marie Brachet-Botineau, Luynes (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE—CNRS—, Paris (FR); UNIVERSITE D'ANGERS, Angers (FR); CENTRE HOSPITALIER UNIVERSITAIRE D'ANGERS, Angers (FR)

( * ) Notice: Subject to any disclaimer, the term of this patent is extended or adjusted under 35 U.S.C. 154(b) by 755 days.

(21) Appl. No.: 17/274,918

(22) PCT Filed: Sep. 16, 2019

(86) PCT No.: PCT/EP2019/074739
§ 371 (c)(1),
(2) Date: Mar. 10, 2021

(87) PCT Pub. No.: WO2020/053445
PCT Pub. Date: Mar. 19, 2020

(65) Prior Publication Data
US 2022/0054424 A1    Feb. 24, 2022

(30) Foreign Application Priority Data
Sep. 14, 2018  (EP) .................... 18306201

(51) Int. Cl.
*A61K 9/51* (2006.01)
*A61K 31/282* (2006.01)
*A61P 35/00* (2006.01)

(52) U.S. Cl.
CPC .......... *A61K 9/5161* (2013.01); *A61K 9/5146* (2013.01); *A61K 9/5192* (2013.01); *A61K 31/282* (2013.01); *A61P 35/00* (2018.01)

(58) Field of Classification Search
CPC .................................................. A61K 9/5161
See application file for complete search history.

(56) References Cited

U.S. PATENT DOCUMENTS

| | | | |
|---|---|---|---|
| 9,320,809 B2 * | 4/2016 | Haam ................. | A61K 47/645 |
| 2012/0177728 A1 | 7/2012 | Lee et al. | |
| 2012/0177742 A1 * | 7/2012 | McClain ................ | A61L 29/16 |
| | | | 424/490 |
| 2015/0118322 A1 | 4/2015 | Lo et al. | |
| 2016/0022824 A1 * | 1/2016 | Haam ................ | A61K 47/6939 |
| | | | 514/19.5 |
| 2016/0361268 A1 * | 12/2016 | Liu ........................ | A61P 35/04 |

FOREIGN PATENT DOCUMENTS

WO      2017120193 A1    7/2017

OTHER PUBLICATIONS

International Search Report and Written Opinion issued on Dec. 4, 2019 in corresponding International Application No. PCT/EP2019/074739; 8 pages.
Felipe a Oyarzun-Ampuero et al: "A new drug nanocarrier consisting of polyarginine and hyaluronic acid", European Journal of Pharmaceutics and Biopharmaceutics, Elsevier Science Publishers B. V., Amsterdam, NL, vol. 79, No. 1, Apr. 18, 2011, pp. 54-57, 4 pgs.
Brown et al., "Gold Nanoparticles for the Improved Anticancer Drug Delivery of the Active Component of Oxaliplatin", J. Am. Chem. Soc., Published on Web Mar. 12, 2010, 132, 4678-4684, 7 pgs.
Oyazur-Ampuero et al., "A new drug nanocarrier consisting of polyarginine and hyaluronic acid", European Journal of Pharmaceutics and Biopharmaceutics, 2011, Available online Apr. 27, 2011, 79(1):54-57, 4 pgs.
Kim et al., "Hyaluronic acid complexed to biodegradable poly L-arginine for targeted delivery of siRNAs", The Journal of Gene Medicine Research Article J Gene Med 2009; 11: 791-803 . . . Published online Jun. 30, 2009 in Wiley InterScience, 13 pgs.
Cabral et al., "Preparation and biological properties of dichloro(1,2-diaminocyclohexane)platinum(II) (DACHPt)-loaded polymeric micelles", Journal of Controlled Release, 101 (2005), Available online Oct. 7, 2004, 223-232, 10 pgs.
Marmiroli P. et al., "Susceptibility of different mouse strains to oxaliplatin peripheral neurotoxicity: Phenotypic and genotypic insights", PLoS One, Oct. 11, 2017, 25 pgs.

(Continued)

Primary Examiner — Gina C Justice
(74) Attorney, Agent, or Firm — Maier & Maier, PLLC

(57) ABSTRACT

The treatment of cancer using platinum-based compounds includes certain drawbacks such as biocompatibility, loading efficacy, leakage of drugs during storage and in the bloodstream, more particularly due to the nature of the nanocarriers for platinum delivery. A nanosystem that allows improving platinum-based drug in vivo performance, kinetics and efficacy. In particular, nanoparticles useful as drug delivery system, these nanoparticles being formed from at least: (a) platinum-based drug, (b) poly-L-arginine, and (c) hyaluronic acid. Particularly, these nanoparticles have been tested in terms of entrapment efficiency and also carried out in vitro experiments in 2D cell culture (viability studies on B6KPC3, A549 and HT-29 cells) and 3D cell model (spheroids made of HTC-116) and in vivo experiments (by injecting intravenously to mice the nanoparticles or comparative oxaliplatin solution) to prove their efficiency.

25 Claims, 6 Drawing Sheets

(56) References Cited

OTHER PUBLICATIONS

Cisterna A et al., "Targeted nanoparticles for colorectal cancer", Nanomedicine (Lond). Published online: Aug. 16, 2016, 14 pgs.

Virgone-Carlotta A, Lemasson M, Mertani HC, et al., "In-depth phenotypic characterization of multicellular tumor spheroids: Effects of 5-Fluorouracil" PLOS One, Nov. 15, 2017, 12(11), 18 pgs.

Hang et al., "Platinum-based anticancer drugs encapsulated liposome and polymeric micelle formulation in clinical trials" Biochemical Compounds, 2016, vol. 4, Article 2, 10 pgs.

Senzer et al., "MBP-426, a novel liposome-encapsulated oxaliplatin, in combination with 5-FU/leucovorin (LV): Phase I results of a Phase I/II study in gastro-esophageal adenocarcinoma, with pharmacokinetics" Molecular Cancer Therapeutics, 2009, 2 pgs, Abstract attached.

* cited by examiner

A

B

C

DRUG DELIVERY SYSTEM

FIELD

The present invention concerns the nanomedicine field for anticancer therapy and proposes novel nanoparticles entrapping at least a platinum-based drug. The present invention also relates to a method for the preparation of these nanoparticles, pharmaceutical compositions comprising these nanoparticles as well as the therapeutic uses of these nanoparticles.

BACKGROUND

During the last decades, the drug delivery research has known an impressive growth in the nanomedicine field for anticancer therapy. Nanomedicine products hold great promise to improve therapeutic strategies due to their ability to improve the performances of the drugs in terms of bioavailability and therapeutic efficacy by targeted delivery of drugs in a tissue- or cell-specific manner and to reduce toxicity.

For obvious reasons, targeted delivery of drugs is particularly advantageous for tumors and/or cancers which are hardly accessible to surgery and nearly impervious to current chemotherapeutic drugs. For example, Pancreatic Ductal Adenocarcinoma (PDAC) is the most common form of pancreatic cancer and its location at the head of the pancreas makes this kind of tumor look like an impregnable fortress.

Two main approaches, "passive" and "active" targeting, have been considered to increase the selectivity of nanomedicine to tumors. Passive targeting benefits from the EPR (Enhanced permeation and retention) effect thanks to the aberrant vascular architecture and poor lymphatic draining. Active targeting uses affinity ligands such as antibodies, vitamins, targeting peptides or overexpression of certain receptors (namely CD44) to target tumors.

Among the drugs considered for treatment of tumors and/or cancers, platinum-based drugs, for instance platinum (II) compounds such as cisplatin, carboplatin and oxaliplatin are approved worldwide.

The clinical trials database maintained by the U.S. National Institutes of Health (NIH), which lists >186 000 clinical trials in over 180 countries, cites cisplatin as a component in more active clinical trials than any other anticancer agent. Similar trends hold for the European Union Clinical Trial Register, which is maintained by the European Medicines Agency (EMA) and lists over 25 000 trials with a European clinical trials database (EudraCT) protocol, as well as the International Clinical Trials Registry Platform of the WHO.

These active agents are important components of chemotherapy but are limited by severe dose-limiting side effects and the ability of tumours to develop resistance rapidly especially in the case of cisplatin. Cisplatin exerts the most toxic effects on organs, such as the nervous system, the organ of Corti and the kidneys, in a dose-dependent fashion among the clinically established platinum compounds. Carboplatin and oxaliplatin are not nephrotoxic in conventional doses. In addition, both drugs are only moderately emetogenic, in contrast to cisplatin. The most important dose-limiting adverse effect of oxaliplatin is a sensory peripheral neuropathy. Moreover, severe anaphylaxis has been reported following the treatment with oxaliplatin. The term "oxaliplatin-induced hypersensitivity reaction" can refer to either acute neurosensory symptoms, a cytokine release syndrome related to increased plasma concentrations of IL-6 and TNF-α or an immunological reaction involving antibody formation and histamine release.

Regarding the mechanisms of actions of platinum based compounds, it involves four key steps: (i) cellular uptake, (ii) aquation/activation, (iii) DNA binding, and (iv) cellular processing of DNA lesions leading to cell death.

Cisplatin undergoes hydrolysis (aquation) within the cell producing a highly reactive charged platinum complex $[Pt(NH_3)_2ClH_2O]^+$. Aquation mostly occurs in the cytoplasm while in the bloodstream such activation is suppressed. After further hydrolysis, this complex binds to DNA bases through the N7 atom (preferably guanine). This DNA cross-linkage mechanism interferes with cell division and replication. The damaged DNA initiates repair mechanisms, which, if unsuccessful, trigger apoptosis.

Oxaliplatin is used in cisplatin resistant cancers and showed no cross-resistance with cisplatin. Oxaliplatin is an organoplatinum structure in which the platinum atom is complexed with diaminocylohexane (also termed "DACH") and with an oxalate ligand as leaving group. Following aquation, several transient reactive species are formed including monoaquo and diaquo DACH platinum, which covalently bind with macromolecules. Only mono-adducts are formed initially, but eventually oxaliplatin attaches simultaneously to two nucleotide bases resulting in DNA cross-links. These cross-links are formed between the N7 positions of two adjacent guanines (GG), adjacent adenine guanines (AG) and guanines separated by an intervening nucleotide (GNG). They inhibit DNA replication and transcription. Oxaliplatin cytotoxicity is cell cycle non-specific.

As described above, studies on second-generation platinum complexes, designed to reduce the dose-limiting toxicities associated with cisplatin treatment, saw the successful development of carboplatin with markedly reduced incidences of renal toxicity.

The design of third-generation platinum complexes was intended to overcome cellular resistance to cisplatin/carboplatin. Amongst the thousands of platinum complexes designed and evaluated, cis-dichloro(1,2-diaminocyclohexane)platinum(II) ($DACHPtCl_2$, also named dichlorinediaminocyclohexane Platinum), containing the DACH modification at the amine ligands of cisplatin, was recognized as a potent anticancer agent.

Depending on the nature of the ligands, the platinum compounds have different solubility in water. Indeed, for example, the solubility is 6 mg/mL for oxaliplatine, 0.25 mg/mL for $DACHPtCl_2$ which solubility is greatly increased due to the transformation reaction into DACHPt (di-Aqua (1,2-diaminocyclohexane)platinum(II)) performed with silver nitrate $AgNO_3$ (7.5 mg/mL).

Aside from the intrinsic action, which is not completely understood, the vast majority of side effects are often due to a poor specificity in the distribution of the drug which leads to important secondary side effects (see above).

To address the issue of solubility and targeting, many attempts to develop nanocarriers improving the performances of platinum compounds have been described.

The first type of carrier envisioned to encapsulate platinum compounds were liposomes such as those described in Senzer et al. (Mol Cancer Ther. 2009; 8 (Supplement 1):C36-C36), and Hang et al. (Biochem Compd. 2016; 4(1):1).

Other types of carriers for platinum compounds were also studied. For example, polymeric micelles were prepared through polymer-metal complex formation of $DACHPtCl_2$ with poly(ethylene glycol)-poly(glutamic acid) block copolymer in distilled water (cabral et al.: J Control Release.

2005; 101(1-3):223-232 and J Control Release. 2007; 121 (3):146-155.). Lipoplatin™ is a proprietary liposomal formulation of Cisplatin (CPT), an FDA-approved, Aroplatin™ (L-NDDP, AR 726) is a chemotherapeutic platinum analogue cis-(trans-R,R-1,2-diaminocyclohexane) bis (neodecanoato) platinum (II) (NDDP) encapsulated liposomal product commercially available cytotoxic agent.

However, some recurrent drawbacks of nanocarriers for platinum delivery still need to be addressed such as biocompatibility, loading efficacy, leakage of drugs during storage and in the bloodstream.

Moreover, the targeting ability could prevent an indiscriminate systemic distribution and accumulation in non-targeted tissue, therefore preventing the apparition of platinum compounds side effects such as neurotoxicity (neuropathy), visual disturbances, ototoxicity or myelosuppression.

Based on these facts, nanoparticular system are prone still to improve platinum-based drugs, in particular platinum(II)-based drugs and/or platinum(IV)-based drugs, preferably platinum(II)-based drugs such as DACHPt in vivo performances, kinetics and efficacy.

Thus, there remains a need in the art to provide anticancer products which are able to improve the efficiency of the drugs like platinum compounds, in particular platinum(II)-based drugs and/or platinum(IV)-based drugs, preferably platinum(II)-based drugs such as DACHPt, in terms of entrapment efficiency, improved bioavailability, enhancement of therapeutic efficacy by targeted delivery of drugs to malignant cells while minimizing exposure to healthy tissue, and reduced toxicity.

There remains also a need in the art to provide anticancer drugs comprising nanocarriers which are biocompatible and biodegradable while being compatible with the platinum-based drugs, in particular platinum(II)-based drugs and/or platinum(IV)-based drugs, preferably platinum(II)-based drugs such as DACHPt.

There remains also a need in the art to provide anticancer drugs comprising nanocarriers which are not mandatorily chemically synthetized.

There remains also a need in the art to provide anticancer drugs which are stable and which can be formulated under the form of ready-to-use lyophilized nanoparticles.

SUMMARY

The present invention relates to nanoparticles useful as drug delivery system, said nanoparticles being formed from at least: (a) platinum-based drug, (b) poly-L-arginine, and (c) hyaluronic acid.

The present invention also concerns a method for preparing said nanoparticles, nanoparticles obtainable by said method, pharmaceutical composition comprising at least one of said nanoparticles and at least one pharmaceutically acceptable excipient, and said nanoparticles for use in the prevention and/or treatment of cancer.

DETAILED DESCRIPTION

Figure 1:
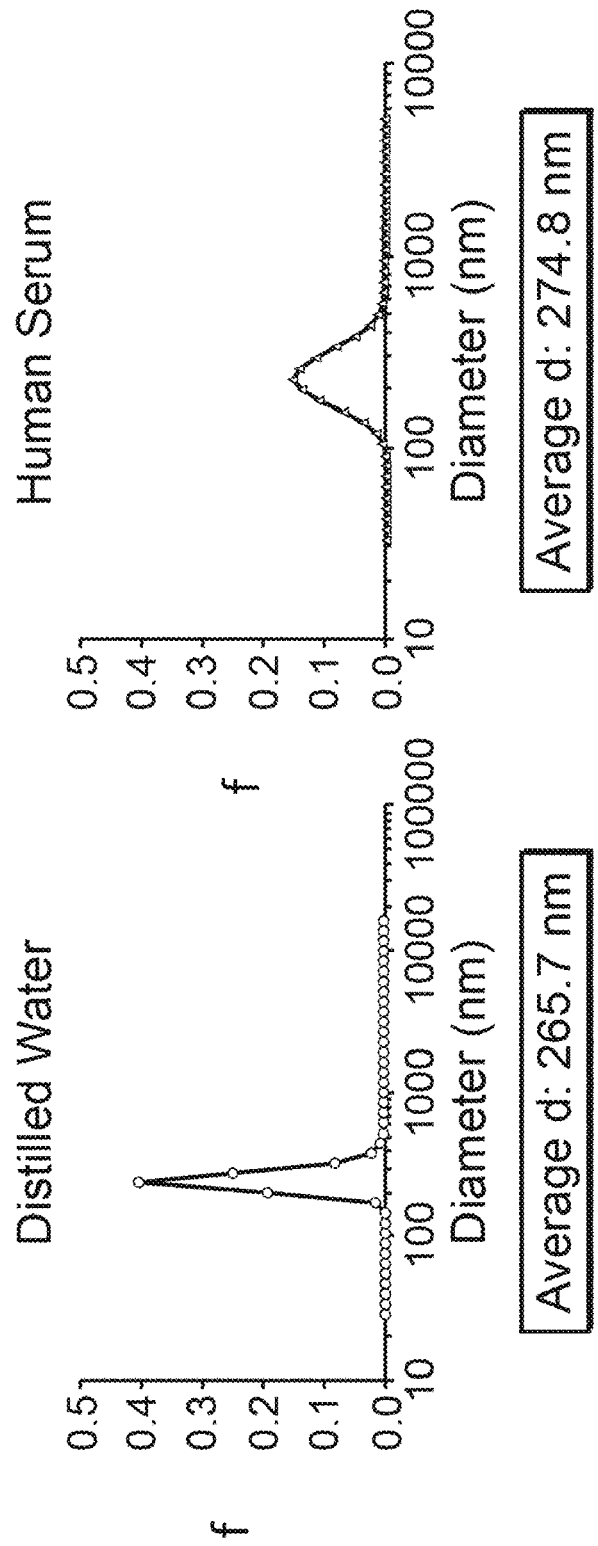
FIG. 1 illustrates SPT (Single Particle Tracking) measurements of Fluorescently labeled PArg-HA nanoparticles following 1 hour incubation in distilled water and human serum.

The present inventors have conceived stable nanoparticles (also named in the present invention NP) allowing efficient incorporation of platinum-based active ingredients and allowing a release of the platinum-based active ingredients according to a pharmacokinetic profile ensuring an optimal therapeutic activity, and especially allowing an optimal anticancer activity.

More precisely, the inventors have conceived nanoparticles comprising a combination of (i) a platinum-based drug, (ii) poly-L-arginine and (iii) hyaluronic acid, which nanoparticles entrap therapeutically effective amounts of a platinum-based drug, which platinum-based drug may be selected among a variety of platinum-based drugs having distinct structures and/or physio-chemical properties, such as, among others, cisplatin, and DACHPt.

Moreover, the platinum-containing nanoparticles provided by the present disclosure allow a release of the entrapped platinum-based according to a pharmacokinetic profile ensuring an optimal therapeutic effect of the said active ingredient. As shown in the examples herein, the said nanoparticles allow obtaining highly increased AUC values of the entrapped platinum-based drug, as compared with the same drug which is not-entrapped.

Highly surprisingly for a drug formulation allowing an increased AUC, the nanoparticles described herein also allow an increased C max of the platinum-based drug, as compared with the same drug which is not-entrapped.

Also, entrapping a platinum-based drug in the nanoparticles according to the present disclosure allows substantially increasing the plasmatic blood circulation, as reflected from the distribution half-life, while elimination half-life did not increased in comparison to the oxaliplatin drug solution.

Furthermore, as shown in the examples herein through pharmacokinetic simulation, the said platinum-containing nanoparticles allow avoiding accumulation of the platinum-based drug entrapped therein, whereas steady-state is rapidly reached after their administration. Otherwise said, the platinum-containing nanoparticles according to the present disclosure allow ensuring a high exposure of a platinum-based drug entrapped herein in the absence of drug accumulation. Such a pharmacokinetic profile illustrates that the platinum-containing nanoparticles described herein fully comply with a repeated administration regimen.

Thus, according to a first aspect, the present invention relates to nanoparticles useful as drug delivery system, said nanoparticles being formed from at least:
(a) platinum-based drug,
(b) poly-L-arginine, and
(c) hyaluronic acid.

Thus, the nanoparticles described herein consist of a platinum-based drug delivery system, i.e. a platinum-containing drug delivery system.

In a preferred embodiment, the platinum-based drug is a platinum complex selected from platinum complex (II), platinum complex (IV) and mixtures thereof.

According to some embodiments, the said platinum-based drug of (a) is selected from the group consisting of platinum (II)-based drugs, platinum(IV)-based drugs and mixtures thereof, preferably is a platinum(II)-based drug, still more preferably is DACHPt. A "platinum-based drug" may also be termed "platinum-containing drug" in the present disclosure.

The nanoparticles of the present invention are produced without solvent in an aqueous solution. If the platinum-based drug is under a low soluble form in water, e.g. with chlorine atom(s), it can be transformed in a more aqueous soluble form, e.g. without chlorine atom(s), by eliminating the chlorine atom(s). In case the chlorine form of the platinum-based drug has to be avoided, the presence of chlorine atom(s) in the poly-L-arginine should be avoided.

In some embodiments, the said platinum-based drug of (a) is present under a form which is devoid of chlorine atom, i.e. the said platinum-based drug is chlorine-free.

In the sense of the present invention, the expressions "free from chlorine atom", "devoid of chlorine atom" or "chlorine-free" mean that the said platinum-based drug is devoid of any chlorine atom; otherwise said, the number of chlorine atom(s) which is(are) present in the platinum-based drug of (a) is zero.

According to other embodiments, the said platinum-based drug of (a) contains chlorine atom(s).

According to some embodiments, the said poly-L-arginine of (b) is not under the form of a hydrochloride salt, i.e. the said poly-L-arginine of (b) is devoid of chloride ion, e.g. is chloride ion-free.

In the sense of the present invention, the expressions "free from chloride ion", "devoid of chloride ion" or "chloride ion-free" mean that the said poly-L-arginine, e.g. under a hydrochloride salt form, of (b) does not contain any detectable amount of chloride ion, or alternatively does not contain chloride ion.

According to further embodiments, the said poly-L-arginine of (b) is provided under a form containing chloride ion(s), e.g. the said poly-L-arginine of (b) preferably comprises one chloride ion per monomer unit of arginine residue present in the said poly-L-arginine.

According to still further embodiments, the said poly-L-arginine of (b) is provided under a form which is a mixture of a form free from chloride ion and of a form containing chloride ion(s), preferably a mixture of poly-L-arginine hydrochloride and poly-L-arginine hydroxide.

The nanoparticles of the present disclosure have a simple structure comprising a network of hyaluronic polymers and poly L-arginine which entraps molecules of platinum-based drugs. Thus, the nanoparticles of the present disclosure do not comprise a core-shell structure.

According to some embodiments, said compounds (a), (b) and (c) are non-covalently linked, one to another.

Nanoparticles containing platinum (II) compounds, such as oxaliplatin, are already described, for example, in US2012/0177728 and in Brown et al. (J. Am. Chem. Soc., 2010, 132, 4678). These prior art nanoparticles are respectively lipid-based nanoparticles and gold-based nanoparticles. Thus, these prior art nanoparticles do not comprise hyaluronic acid and polyarginine.

Nanocarriers comprising both hyaluronic acid and polyarginine are known per se in the art, Illustratively, Oyazurn-Ampuero et al. (Eur J Pharm Biopharm Off J Arbeitsgemeinschaft Für Pharm Verfahrenstechnik eV. 2011; 79(1): 54-57) used hyaluronic acid and polyarginine for obtaining nanocarriers and have evaluated the stability of such nanocarriers, which nanocarriers were not loaded with any drug. These authors contemplated further exploring the relevancy of such nanocarriers by loading them with hydrophilic drugs, especially with the view of oral delivery of peptides. Also, Kim et al. (2009, Gene Med, Vol. 11: 791-803) have tested nanoparticles formed by electrostatic complexation of negatively-charged hyaluronic acid and cationic poly L-arginine for siRNA delivery.

According to another aspect, the present invention concerns a method for preparing nanoparticles described herein, the said method comprising at least the steps of:
(i) providing a platinum-based drug under the form of an aqueous complex free from chlorine atom,
(ii) providing an aqueous solution of poly-L-arginine free from chloride ion,
(iii) mixing said platinum-based drug under the form of an aqueous complex of (i) and said aqueous solution of (ii)
(iv) adding hyaluronic acid to the mixture obtained at step (iii) in conditions suitable for forming the nanoparticles, and optionally
(v) recovering the nanoparticles obtained at step (iv).

According to a specific embodiment, the aqueous complex form (i) of the platinum-based drug, free from chlorine atom, is formed by conversion of the dichloride form of the platinum-based drug through a pre-treatment with $AgNO_3$ (silver nitrate).

According to a specific embodiment, the poly-L-Arginine free from chloride ion (ii) is obtained from the poly-L-Arginine hydrochloride (PArg-Cl).

Another subject of the present invention is directed to the nanoparticles thus obtained by said method of preparation.

According to another subject, the present invention is directed to a pharmaceutical composition comprising to least one of the nanoparticles as defined in the present invention and at least one pharmaceutically acceptable excipient.

According to another of its subjects, the present invention relates to the nanoparticles described herein for their use in the prevention and/or treatment of cancer, such as pancreatic cancer, in particular pancreatic ductal adenocarcinoma (PDAC), colorectal cancer, lung cancer, small and non-small cell lung cancer, ovarian cancer, testicular cancer, breast cancer, brain cancer, sarcomas, lymphomas, head and neck cancer, metastatic colorectal cancer, gastric cancer, ovarian cancer, esophageal cancer, bladder cancer, cervix cancer, leukemia such as chronic myeloid leukemia, prostate cancer, liver cancer, colon cancer, renal cancer, skin cancer, bone cancer, uterine cancer, lymphatic cancer, stomach cancer, intestinal cancer.

The present invention also pertains to the nanoparticles described herein for use in the prevention and/or treatment of cancer which usually are cisplatin resistant cancers.

Nanoparticles According to the Invention

As mentioned elsewhere herein, the present invention relates to nanoparticles useful as drug delivery system, said nanoparticles being formed from at least:
(a) platinum-based drug,
(b) poly-L-arginine, and
(c) hyaluronic acid.

According to a specific embodiment, the present invention relates to nanoparticles useful as drug delivery system, said nanoparticles being formed from at least:
(a) platinum-based drug present under a form free from chlorine atom,
(b) poly-L-arginine hydroxide, and
(c) hyaluronic acid.

According to a preferred specific embodiment, the present invention relates to nanoparticles useful as drug delivery system, said nanoparticles being formed from at least:
(a) DACHPt,
(b) poly-L-arginine hydroxide, and
(c) hyaluronic acid.

In the specific embodiment in which DACHPt is used as the platinum-based drug of (a), the use of poly-L-arginine hydroxide (instead of poly-L-arginine hydrochloride or instead of a mixture of poly-L-arginine hydroxide and poly-L-arginine hydrochloride) as the poly-L-arginine of (b) allows advantageously avoiding formation of DACHPtCl2 which precipitates as it is not water-soluble. The presence of DACHPtCl$_2$ would greatly hampers the formation of drug-loaded nanoparticles according to the present invention.

According to another specific embodiment, the present invention relates to nanoparticles useful as drug delivery system, said nanoparticles being formed from at least:
(a) platinum-based drug containing chlorine atom(s).
(b) poly-L-arginine hydrochloride, and
(c) hyaluronic acid.

According to a preferred specific embodiment, the present invention relates to nanoparticles useful as drug delivery system, said nanoparticles being formed from at least:
(a) cisplatin,
(b) poly-L-arginine hydrochloride, and
(c) hyaluronic acid.

In the specific embodiment in which cisplatin is used as the platinum-based drug of (a) and in which poly-L-arginine hydrochloride is used as the poly-L-arginine of (b), the advantages are especially the protection of the drug from plasma proteins and a more specific accumulation of the drug in the tumor(s).

The nanoparticles according to the invention form a polymeric nanosystem with a matrix system.

The nanoparticles according to the invention are spherical.

More particularly, the nanoparticles according to the invention are entrapping (associating) the platinum-based drug in their matrix.

For example, it is assumed that said DACHPt nanoparticles are formed based on electrostatic complexation of negatively charged HA and cationic poly-L-arginine under a form free from chloride ion, such as PArg-OH, in aqueous solutions. Based on this hypothesis, platinum-based drug, poly-L-arginine and hyaluronic acid are non-covalently coupled to each other Loaded nanoparticles according to the invention have a mean size, i.e. an hydrodynamic size, before freeze-drying less than or equal to 200 nm, preferably ranging from 100 nm to 200 nm, more preferably from 130 nm to 180 nm, measured using a Malvern Zetasizer® apparatus DTS 1060 (Nano Series ZS, Malvern Instruments S.A., Worcestershire, UK) at 25° C., in triplicate, after a 1/60 dilution of nanoparticles dispersions with deionized water.

As shown in the experimental part, platinum-based drug-loaded nanoparticles such as DACHPt-loaded nanoparticles are smaller than the corresponding blank systems (that is to say non-loaded nanoparticles). It may be suggested that this difference was due to a different rearrangement of the polymeric chains in presence of the drug. The main force driving the association of DACHPt is assumed to be the interaction between positive charges from the platinum and negative carboxylic groups coming from HA.

Further, the nanoparticles according to the invention present a zeta potential (ZP) before freeze-drying ranging from −50 to −10 mV, preferably from −47 to −27 mV, measured using a Malvern Zetasizer® apparatus DTS 1060 (Nano Series ZS, Malvern Instruments S.A., Worcestershire, UK) at 25° C., in triplicate, after a 1/60 dilution of nanoparticles dispersions with deionized water.

Furthermore, the nanoparticles according to the invention possess a polydispersity index (PDI) before freeze-drying lower than or equal to 0.20, preferably ranging from 0.01 to 0.20, more preferably from 0.03 to 0.06.

Besides, the nanoparticles according to the present invention, in particular in the form of a lyophilisate, are particularly advantageous.

Indeed, once the lyophilized (or freeze-dried) powder of nanoparticles is reconstituted with purified water, the pH and the osmolarity of the suspension are perfectly compatible, for example, with an intravenous (IV) injection.

Moreover, the freeze-dried powder has an increased shelf-life. This result is very advantageous compared to previous formulations such as micelles which size remained stable for 240 hours only.

Thus, according to a particular embodiment, the nanoparticles according to the invention are lyophilized. The freeze-drying process can be performed using an ALPHA 1-4 LSC (CHRIST) freeze dryer equipped with an RZ6 Vacubrand pomp (Fisher Scientific, Illkirch, France). A ready-to-use stable lyophilized form of nanoparticles is thus obtained.

After freeze-drying, the size, polydispersity, and zeta potential of these nanoparticles can be also evaluated, after resuspension of the powder in water, with the same methods and apparatuses as explained above before freeze-drying. The respective ranges of values are defined below.

The nanoparticles according to the invention have a mean size, i.e. hydrodynamic size, after freeze-drying, less than or equal to 300 nm, preferably ranging from 100 nm to 300 nm, and in particular from 200 nm to 300 nm.

Hence, it comes out from the above and as demonstrated in the examples, the mean size, i.e. hydrodynamic size, of the nanoparticles according to the invention is slightly increased after freeze-drying. This variation is not linked to a loss of stability of the system.

Furthermore, the nanoparticles according to the invention possess a polydispersity index (PDI) after freeze-drying lower than or equal to 0.20, preferably ranging from 0.010 to 0.200, and in particular from 0.050 to 0.150, or even from 0.054 to 0.133.

As shown in the experimental part, the value of the PDI characteristic for said nanoparticles before or after freeze-drying indicates that the population of the obtained nanoparticles is quite homogeneous and monodispersed.

The shape and size around 200 nm and the low polydispersity (PDI lower than 0.2) of the formulation presuppose extravasation and diffusion leading to tumor accumulation in vivo.

Further, the nanoparticles according to the invention present an entrapment efficiency ranging from 35% to 90%, preferably from 40% to 80%, more preferably from 42% to 75%.

The high entrapment efficiency assuming a good targeting of the system presuppose an increased efficiency of the drug for the same administered dose.

The mechanisms underlying the association of the platinum-based drug, in particular platinum(II)-based drug with the polymer resides in the complexation between the platinum-based drug, the HA and the PArg. The carboxylic functions of the HA negatively charged ($COO^-$) binds with the positive charges of the platinum metallic ion and of the PArg, the interaction induces a reticulation of the polymers leading to the formation of the nanoparticular complex.

The negative surfaces charges of the particles obtained with the different [HA]/[PArg] weight ratios, indicate that there is a predominance of HA at the surface of the particle. The biocompatibility of the polymer combined to the negative charges presuppose a facilitated circulation in blood and limited uptake by the macrophages of reticuloendothelial system.

The main advantage of this formulation relies on the fact that no organic solvent is required thereby avoiding product degradation and facilitating the production process. Comparing the nanoparticles in accordance with the invention with the micelles developed by Cabral et al (*J Control Release.* 2005; 101(1-3):223-232), the polymers used to formulate HA/PArg nanoparticles are pharmaceutically acceptable and did not require chemical modifications.

For example, when the platinum-based drug is di-aqua(1, 2-diaminocyclohexane)platinum (II) (DACHPt: the active form of Oxaliplatin), the stability of the freshly formulated nanoparticles is around 2 weeks in solution in terms of size, as oxaliplatin degradation occurs after 14 days.

To address this issue, the polymer solutions are prepared in a mannitol 10% (w/w) solution acting as cryoprotectant. The stability in terms of size and entrapment efficacy is assured for around 1 month. Final mannitol concentration in the nanoparticles is around 7% (w/w).

Composition of Nanoparticles

The nanoparticles according to the invention form a polymeric nanosystem prepared from a hyaluronic acid (HA) and poly-L-arginine to entrap (or associate) platinum-based drug, in particular platinum(II)-based drug such as di-aqua(1,2-diaminocyclohexane)platinum (II).

a) Platinum-Based Drugs

As mentioned above, among platinum-based drugs suitable for the present invention may be cited platinum(II)-based drugs, platinum(IV)-based drugs, and mixtures thereof.

As platinum(II)-based drugs may be cited for example DACHPt, cisplatin, oxaliplatin, carboplatin, nedaplatin, lobaplatin, heptaplatin.

As platinum(IV)-based drugs may be cited for example satraplatin.

According to a specific embodiment, said platinum-based drug of (a) is present under a form free from chlorine atom.

According to a preferred specific embodiment, said platinum-based drug of (a) which is free from chlorine atom is a platinum(II)-based drug.

According to a more preferred specific embodiment, said platinum-based drug of (a) which is free from chlorine atom is selected from the group consisting of DACHPt, oxaliplatin, carboplatin, nedaplatin, lobaplatin, heptaplatin, cis-diamminediaquaplatinum(II), di-aqua(1,2-diaminomethyl)cyclobutane)platinum(II), di-aqua(4,5-diaminomethyl-2-isopropyl-1,3-dioxolane)platinum(II) and mixtures thereof.

According to a still more preferred specific embodiment, said platinum-based drug of (a) which is free from chlorine atom is DACHPt.

According to another specific embodiment, said platinum-based drug of (a) contains chlorine atom(s).

According to a preferred specific embodiment, said platinum-based drug of (a) which contains chlorine atom(s) is selected from the group consisting of a platinum(II)-based drug and a platinum(IV)-based drug.

According to a more preferred specific embodiment, said platinum-based drug of (a) which contains chlorine atom(s) is selected from the group consisting of cisplatin and satraplatin.

According to a still more preferred specific embodiment, said platinum-based drug of (a) which contains chlorine atom(s) is cisplatin.

Cisplatin (CDDP, (cis-diamminedichloroplatinum(II))) was the first member of classical platinum complexes. The platinum atom is complexed to two chlorine atoms and to two $NH_3$ groups as ligands.

Carboplatin (cis-diammine(1,1-cyclobutanedicarboxylato)platinum(II)) is a second-generation platinum drug. In Carboplatin, the two chlorine atoms (present in cisplatin) were replaced by oxygenated ligands which come from a C3 dicarboxylic acid, the central carbon atom of which forming with three other carbon atoms a cyclobutyl ring.

Nedaplatin (cis-diammineglycolatoplatinum(II)) is a second-generation platinum drug.

Oxaliplatin is a third-generation platinum drug which is an organic complex consisting of platinum and 1,2-diaminocyclohexane («DACH») and having an oxalate ligand as a leaving group (1,2-diaminocyclohexane platinum(II) oxalate). Its IUPAC name is (R,R)-1,2-diaminocyclohexane (ethanedioato-O,O)platinum. Currently, oxaliplatin is marketed for treatment of advanced colorectal cancer and metastatic stomach cancer under the brand of Eloxatin® by Sanofi. Frequently, it is administered with 5-fluorouracil (5-FU) and/or folinate salts (leucoverin) (FOLFOX or FOLFIRI).

The activity of oxaliplatin as an anticancer drug involves multiple pathways. The main effect resides in the capacity of the Platinum atom to bind DNA and form simple or double strands by linking guanines, rending impossible the proliferation of the cells and leading to their death. Upon entering the cell, oxaliplatin undergoes hydrolysis in which the oxalate moieties are exchanged with chlorine ions. This results in the formation of dichlorinediaminocyclohexane Platinum ($DACHPtCl_2$). A final hydrolysis activates the drug in the form of a di-Aqua(1,2-diaminocyclohexane) platinum(II).

Lobaplatin, a third-generation platinum drug, is a chelate formed from lactic acid. Its chemical name is cis-[(1R*, 2R*)-1,2-Cyclobutanebis(methylamino)-N,N'][(2S)-2-hydroxypropanoato(2-)-O1,O2]platinum.

Heptaplatin is a platinum malonate complex which chemical name is cis-malonato(4,5-bis(aminomethyl)-2-isopropyl-1,3-dioxolane)platinum(II). It is also a third-generation platinum drug.

As Platinum (IV) compounds may be more particularly cited satraplatin.

The platinum-based drugs suitable for the present invention may be present un the nanoparticles of the present disclosure in an amount which may greatly vary, depending on the kind of platinum-based drug which is comprised therein. Indeed, the one skilled in the art, on the basis of the abundant literature relating to the platinum-based drugs, knows determining the appropriate amount of platinum-based drug to be entrapped within the nanoparticles.

The platinum-based drugs suitable for the present invention are present in an amount ranging from 0.0001 percent by weight to 15 percent by weight, preferably from 0.001 percent by weight to 10 percent by weight, more preferably from 0.001 percent by weight to 1 percent by weight, relative to the total weight of the nanoparticles.

b) Poly-L-Arginine (PArg)

Conventionally, poly-L-arginine is used under its hydrochloride form, the poly-L-arginine hydrochloride (PArg-Cl). It's more often the Poly-L-Arginine hydrochloride (Mw ranging from 5 kDa to 100 kDa, preferably from 5 kDa to 15 kDa, or preferably from 50 kDa to 100 kDa, or preferably from 20 kDa to 50 kDa) marketed by Alamanda™ Polymers.

It is a positively charged synthetic polyamino acid having one HCl per arginine unit. It is a crystalline solid soluble in water. Its safety profile is very interesting with a behavior similar to the polypeptides in terms of degradation by human enzymes and therefore minimal accumulation within the organism.

According to a specific embodiment, said poly-L-arginine of (b) is provided under a form containing chloride ion(s), that is to say one chloride ion (or one HCl) per arginine unit present in the polymer.

According to a preferred specific embodiment, said poly-L-arginine of (b) which is provided under a form containing chloride ion(s), is poly-L-arginine hydrochloride.

According to another specific embodiment, said poly-L-arginine of (b) is provided under a form free from chloride ion.

According to a preferred specific embodiment, said poly-L-arginine of (b) which is provided under a form free from chloride ion is poly-L-arginine hydroxide (PArg-OH).

According to another specific embodiment, said poly-L-arginine of (b) is provided under a form which is a mixture of a form free from chloride ion and of a form containing chloride ion(s), preferably a mixture of poly-L-arginine hydrochloride and poly-L-arginine hydroxide.

In the nanoparticles according to the present invention, the weight ratio of poly-L-arginine hydrochloride to poly-L-arginine hydroxide can range from 0/100 to 100/0, in particular can be 0/100, 25/75, 50/50, 75/25 or 100/0.

It is to be understood, that for example when the weight ratio of poly-L-arginine hydrochloride to poly-L-arginine hydroxide is 0/100, this means that the poly-L-arginine of (b) is exclusively poly-L-arginine hydroxide or when the weight ratio of poly-L-arginine hydrochloride to poly-L-arginine hydroxide is 100/0, this means that the poly-L-arginine of (b) is exclusively poly-L-arginine hydrochloride.

The PArg-OH can be prepared by modifying the PArg-Cl with an ion exchange resin by adding a base such as NaOH to the column containing the resin. The so-obtained Poly-L-Arginine, PArg-OH is then recovered at the bottom of the column.

Preferably, the PArg-OH considered according to the invention has a weight average molecular weight (Mw), preferably ranging from 3 000 to 17 000 Daltons, preferably from 5 000 to 15 000 Daltons.

The poly-L-arginine of (b) according to the invention is present in an amount ranging from 2% to 30% by weight, preferably from 5% to 20% by weight, more preferably from 10% to 17% by weight relative to the total weight of the nanoparticles.

c) Hyaluronic Acid (HA)

Hyaluronic acid (also called hyaluronan or hyaluronate) is an anionic polysaccharide composed of disaccharide units containing N-acetyl-D-glucosamine and D-glucuronic acid naturally present in the human body (biological fluid and tissues) and widely used in pharmacy.

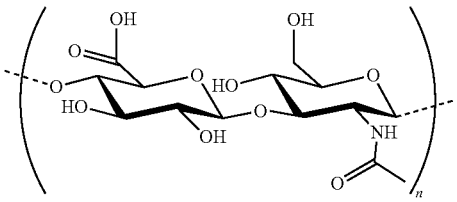

HA is also non-toxic, mucoadhesive and biodegradable.

Moreover, HA possesses an intrinsic targeting activity, as it acts as an affinity ligand towards CD44. CD44 is expressed on tumor cells and overexpressed on some resistant cell lines and in cancer stem cells, especially after treatment with some anticancer drugs such as Gemcitabine.

Further, advantageously, the tumoral microenvironment is often rich in hyaluronidase, which could induce a greater liberation of the drug in situ.

The hyaluronic acid according to the invention has a weight average molecular weight (Mw) ranging from 10 kDa to 100 kDa, preferably from 10 kDa to 30 kDa, preferably from 15 kDa to 25 kDa, more preferably is 20 kDa, or preferably from 50 kDa to 100 kDa.

All number herein expressing "molecular weight" of hyaluronic acid are to be understood as indicating the weight average molecular weight (Mw) in Daltons (Da).

Among hyaluronic acid suitable for the present invention can be cited hyaluronic acid (HA, LMWHA (Mw 20 kDa)) marketed by Lifecore Biomedical.

The hyaluronic acid according to the invention is present in an amount ranging from 2.5% to 12% by weight, preferably from 4% to 12% by weight relative to the total weight of the nanoparticles.

As shown in the experimental part, when [HA]/[PArg] mass ratio is under 0.5/2.5, nanostructures with a positive zeta potential are obtained, indicating that the surface of these systems could be composed mainly of positively charged PArg. Above this ratio, the organization is reversed and HA chains were exposed on the surface. In the case of drug-loaded nanostructure, from the ratio of 7/2.5 to 12/2.5 no difference in terms of size is observed, suggesting that the system is stable and further addition of HA does not induce any change in the association.

Thus, the [HA]/[PArg] weight ratio (or mass ratio) of these nanoparticles is higher than 0.5/2.5 (=0.2), preferably ranging from 0.6/2.5 (=0.24) to 15/2.5 (=6), more preferably from 3/2.5 (=1.2) to 12/2.5 (=4.8), for example 3/2.5, 4/2.5 (=1.6), 7/2.5 (=2.8), 9/2.5 (=3.6), 10/2.5 (=4), 11.25/2.5 (=4.5), and 12/2.5, still more preferably is 11.25/2.5.

Furthermore, the [platinum-based drug]/[HA]+[PArg] weight ratio (or mass ratio) of these nanoparticles is ranging from 0.01 to 1.00, preferably from 0.03 to 0.50, more preferably from 0.04 to 0.10.

According to a preferred embodiment, the nanoparticles useful as drug delivery system according to the invention are formed from at least:
(a) platinum(II)-based drug,
(b) poly-L-Arginine, and
(c) hyaluronic acid.

According to a more preferred embodiment, the nanoparticles useful as drug delivery system according to the invention are formed from at least:
(a) di-aqua(1,2-diaminocyclohexane)platinum (II),
(b) poly-L-Arginine, and
(c) hyaluronic acid.

According to a still more preferred embodiment, the nanoparticles useful as drug delivery system according to the invention are formed from at least:
(a) di-aqua(1,2-diaminocyclohexane)platinum (II),
(b) poly-L-Arginine hydroxide, and
(c) hyaluronic acid.

As shown in the examples, the nanoparticles according to the invention are stable, even after freeze-drying, particularly in terms of size, and also under biological conditions.

Besides, as shown in the experimental part and more particularly, in the in vitro experiments it was demonstrated that the non-loaded nanocarriers are non-toxic to the tested cell line, which is promising for an in vivo use.

The comparison of IC50 between the free drugs and the loaded nanoparticles demonstrated that the cytotoxic effect was superior for the free drugs.

In the present invention, hydrodynamic size and polydispersity index (PDI) of nanoparticles were determined by Dynamic Light Scattering (DLS). Samples were diluted to an appropriate concentration in deionized water and each analysis was carried out at 25° C. with a detection angle of 173°.

In the present invention, the zeta potential (ZP) values were calculated from the mean electrophoretic mobility values, as determined by Laser Doppler Anemometry (LDA). For LDA measurements, previously diluted samples were used and placed in an electrophoretic cell.

DLS and LDA analyses were realized in triplicate using a NanoZS® (Malvern Instruments S.A., Worcestershire, United Kingdom).

Method for the Preparation of Nanoparticles According to the Invention

As mentioned above; the present invention relates to a method for preparing nanoparticles according to the present invention, said method comprising at least the steps of:
(i) providing a platinum-based drug under the form of an aqueous complex free from chlorine atom,
(ii) providing an aqueous solution of poly-L-arginine free from chloride ion,
(iii) mixing said platinum-based drug under the form of an aqueous complex of (i) and said aqueous solution of (ii)
(iv) adding hyaluronic acid to the mixture obtained at step (iii) in conditions suitable for forming the nanoparticles, and optionally
(v) recovering the nanoparticles obtained at step (iv).

This method of preparation is an improved ionotropic gelation method as explained below. The general procedure of the ionotropic gelation method is for example described in Oyarzun-Ampuero et al. (Eur J Pharm Biopharm Off J Arbeitsgemeinschaft Für Pharm Verfahrenstechnik eV. 2011; 79(1):54-57).

According to a specific embodiment, the present invention concerns a method for preparing nanoparticles according to the present invention, said method comprising at least the steps of:
(i) providing DACHPt,
(ii) providing an aqueous solution of poly-L-arginine hydroxide,
(iii) mixing said DACHPt of (i) and said aqueous solution of (ii)
(iv) adding hyaluronic acid to the mixture obtained at step (iii) in conditions suitable for forming the nanoparticles, and optionally
(v) recovering said nanoparticles obtained at step (iv).

Advantageously, the method of preparation according to the invention allows to provide stable platinum-based drug nanoparticles, in particular platinum(II)-based drug nanoparticles by rendering the platinum-based drug, in particular platinum(II)-based drug aqueous complex compatible with the chlorides optionally present in the polyarginine solution.

Step (i)

In the step (i), a platinum-based drug under the form of an aqueous complex free from chlorine atom is provided.

Such a platinum-based drug under the form of an aqueous complex can be obtained by any process known by the skilled person.

For example, this aqueous complex can be prepared via the conversion of a dichloride form of said platinum-based drug by a pretreatment with silver nitrate ($AgNO_3$). This step has already been described, for example, in Oberoi et al.[18].

The dichloride form of said platinum-based drug such as $DACHPtCl_2$, is suspended in distilled water and mixed, for instance under magnetic stirring, with silver nitrate ([$AgNO_3$]/[dichloride form of said platinum-based drug]=1) in the dark at room temperature (25° C.) for a duration of from 1 h to 48 h, preferably from 10 h to 24 h, and more preferably of 24 h to form the corresponding aqueous complex.

Among the dichloride forms of platinum-based drugs can be cited diaminedichloroplatinum(II) (cisplatin), dichloro(1,2-diaminocyclohexane)platinum(II) ($DACHPtCl_2$), dichloro (1,2-diaminomethyl)cyclobutane)platinum(II), dichloro(4,5-diaminomethyl-2-isopropyl-1,3-dioxolane)platinum(II), and mixtures thereof.

Preferably, the dichloride form of platinum-based drug is dichloro(1,2-diaminocyclohexane)platinum(II).

Dichloro(1,2-diaminocyclohexane)platinum(II) can be, for example, the $DACHPtCl_2$ (Mw=380.17 Da) provided by Sigma Aldrich.

After reaction, silver chloride (AgCl) precipitates are formed.

Afterwards, these AgCl precipitates are removed by centrifugation at 3000 rpm, for a duration of from 10 min to 20 min and more preferable of 20 min.

Then, the supernatant is purified by filtration through a 0.22 μm filter and the corresponding aqueous complex is thus recovered.

Thus, the corresponding platinum-based drug under the form of an aqueous complex free from chlorine atom can be chosen among diaminediaquaplatinum(II), di-aqua(1,2-diaminocyclohexane)platinum(II) (DACHPt), di-aqua(1,2-diaminomethyl)cyclobutane)platinum(II), di-aqua(4,5-diaminomethyl-2-isopropyl-1,3-dioxolane)platinum(II), and their mixtures and is preferably di-aqua(1,2-diaminocyclohexane)platinum(II).

Step (ii)

The step (ii) consists in the providing of an aqueous solution of poly-L-Arginine free from chloride ion.

According to a specific embodiment, the poly-L-Arginine free from chloride ion is obtained from poly-L-Arginine hydrochloride (PArg-Cl).

According to another specific embodiment, said aqueous solution of poly-L-Arginine free from chloride ion is an aqueous solution of poly-L-Arginine hydroxide (PArg-OH).

For example, poly-L-Arginine hydroxide can be obtained by desalting of poly-L-Arginine hydrochloride (PArg-Cl) by using a base and an ion exchange resin. PArg-Cl is thus modified with an ion exchange resin (column), in particular an anion exchange resin such as the one marketed under the name of Amberlite® IRA 900 Cl by Rohm&Haas.

First, a base is added to the column containing the corresponding wet resin. A base suitable for the present invention can be chosen among NaOH, LiOH, . . . , and mixtures thereof.

After a sufficient time, for example from 15 min to 1 hour, preferably 30 min, the column is rinsed with purified water until the pH of the solution reached a neutral pH.

Then, the PARg-Cl solution, for example, the Poly-L-Arginine hydrochloride (Mw ranging from 5 kDa to 100 kDa, preferably from 5 kDa to 15 kDa, or preferably from 50 kDa to 100 kDa, or preferably from 20 kDa to 50 kDa) marketed by Alamanda™ Polymers, is put on the top of the column. When passing through the column, the chloride ions of PARg-Cl are exchanged with the OH ions contained in the column.

A PArg-OH solution is then recovered at the bottom of the column. Next, this PArg-OH solution is rinsed with purified water until the solution reaches the desired concentration, for example 12.5 mg/mL.

The specific modification of PArg-Cl into PArg-OH allows eliminating residual chlorides (Cl$^-$) that induce the precipitation of the activated platinum-based drugs such as DACHPt into dichloro platinum-based drugs such as DACHPtCl$_2$ which greatly hamper the formation of drug-loaded nanoparticles.

The step (ii) thus allows overcoming the incompatibility problems of the PArg chloride salt with the platinum-based drugs, in particular platinum(II)-based drugs and contributes to obtain afterwards stable nanoparticles.

Step (iii)

The step (iii) corresponds to the mixing of the aqueous complex of platinum-based drug, free from chlorine atom, of step (i) to the aqueous solution of poly-L-Arginine free from chloride ion of step (ii).

The aqueous solution of poly-L-Arginine free from chloride ion such as PArg-OH solution and the aqueous complex of platinum-based drug such as platinum(II)-based drug free from chlorine atom are mixed together, for example, in a vial and are left under stirring for a duration of from 1 min to 20 min, preferably for 10 min.

A mixture of the two above-mentioned components of steps (i) and (ii) is thus obtained.

Step (iv)

In step (iv), hyaluronic acid, for example HA (LMWHA (Mw≈20 kDa)) marketed by Lifecore Biomedical, is added to the mixture obtained from step (iii) so as to obtain the desired nanoparticles.

Advantageously, prior to the mix, the solutions are filtered with a 0.22 μm filter to ensure sterility.

Then, HA is combined to the mixture of said aqueous complex of (i) and said aqueous solution of (ii) obtained from step (iii) by simply mixing polymeric aqueous solutions at room temperature under magnetic stirring so as to lead to the formation of loaded nanoparticles.

Different concentration of HA may be added in step (iv), for example ranging from 2.5 mg/ml to 12 mg/ml, preferably from 0.5 mg/ml to 12 mg/ml. This allows obtaining different [HA/PArg] mass ratio for the nanoparticles and thus can help to determine the contribution of polymers to the nanosystems and to customize the nanoparticles for the incorporation of positively charged hydrophilic molecules such as DACHPt.

Besides, the pH and osmolality are checked for all the formulations which are prepared in presence of mannitol 10% w/v.

At the neutral pH, HA is a negatively charged polysaccharide and PArg is a polyaminoacid presenting positive charges able to form nanoparticles by electrostatic interactions, that is to say by non-covalent bonds.

Step (v)

The step (v) is optional and consists of the isolation of the nanoparticles obtained from step (iv).

To isolate the system, a given volume, for example 1 mL, of nanoparticles suspension is transferred to Eppendorf tubes and centrifuged (for example at 16 000 g, for 30 min, at 25° C.) in a given volume, for example 20 μL, of a glycerol bed.

The supernatants are then discarded, and the nanoparticles are resuspended in water using a pipette and vigorous vortexing.

The method of preparation in accordance with the invention allows obtaining a bioinspired polymeric nanocarrier composed of hyaluronic acid as defined above and polyarginine as defined above.

As shown in the experimental part, this nanostructure can successfully entrap (or associate) a platinum-based drug, in particular platinum(II)-based drug, such as the active form of oxaliplatin, namely DACHPt.

The main force driving the association of platinum-based drug, in particular platinum(II)-based drug such as DACHPt, is assumed to be the interaction between positive charges from the platinum and negative carboxylic groups coming from HA.

Hence, the molecules of a platinum-based drug, in particular platinum(II)-based drug, poly-L-Arginine, and hyaluronic acid are coupled to each other via electrostatic interactions, that is to say via non-covalent bonds.

Advantageously, said method is simple and does not require organic solvents, unlike many carriers reported in the literature until now[17, 25, 39]. It is therefore potentially scalable as the number of steps involved is very limited.

Consequently, due to its simplicity, the method of preparation in accordance with the invention can easily be envisioned in a sterile environment and under GMP (good manufacturing practices) conditions.

Therapeutic Uses

As illustrated in the examples, the nanoparticles as defined in the present invention are able to prevent and/or treat cancer such as pancreatic cancer, in particular pancreatic ductal adenocarcinoma (PDAC), colorectal cancer, lung cancer, small and non-small cell lung cancer, ovarian cancer, testicular cancer, breast cancer, brain cancer, sarcomas, lymphomas, head and neck cancer, metastatic colorectal cancer, gastric cancer, ovarian cancer, esophageal cancer, bladder cancer, cervix cancer, leukemia such as chronic myeloid leukemia, prostate cancer, liver cancer, colon cancer, renal cancer, skin cancer, bone cancer, uterine cancer, lymphatic cancer, stomach cancer, intestinal cancer.

The nanoparticles according to the invention can therefore be used to prepare medicaments, especially medicaments which are useful for preventing and/or treating cancer such as pancreatic cancer, in particular pancreatic ductal adenocarcinoma (PDAC), colorectal cancer, lung cancer, small and non-small cell lung cancer, ovarian cancer, testicular cancer, breast cancer, brain cancer, sarcomas, lymphomas, head and neck cancer, metastatic colorectal cancer, gastric cancer, ovarian cancer, esophageal cancer, bladder cancer, cervix cancer, leukemia such as chronic myeloid leukemia, prostate cancer, liver cancer, colon cancer, renal cancer, skin cancer, bone cancer, uterine cancer, lymphatic cancer, stomach cancer, intestinal cancer.

Accordingly, in another of its aspects, the invention provides medicaments which comprise nanoparticles according to the invention.

These medicaments are employed therapeutically, especially in the treatment and/or the prophylaxis of cancer such as those described above.

Pharmaceutical Compositions and Modes of Administration

According to another of its aspects, the present invention relates to pharmaceutical compositions comprising, as active principle, nanoparticles according to the invention. More particularly, these pharmaceutical compositions contain an effective dose of nanoparticles according to the invention and also at least one pharmaceutically acceptable excipient.

Given the small size of the nanoparticles, they can be administered intravenously (IV or i.v.), subcutaneously (SQ or s.q.), intracutaneously (IC or i.c.), intramuscularly (IM or i.m.), or intraperitoneally (IP or i.p.), preferably intravenously in the form of an aqueous suspension and are therefore compatible with the vascular microcirculation.

Thus, the pharmaceutical composition can be administered parenterally, intravenously, or by any other suitable route.

In one embodiment, the pharmaceutical compositions are administered parenterally by injecting the composition close to the site of a tumor. As used herein, "close to the site of a tumor" is meant to refer to local targeting and delivery of the composition to the site of the tumor and is meant to include direct injection into the tumor as well as injection within about 1 cm (e.g., within 1 cm, within about 5 mm, within 5 mm, within about 2 mm, within 2 mm, etc.) of the tumor. The pharmaceutical composition can be administered, for example, via a single injection or via multiple injections, such as in the case where the pharmaceutical composition is administered by injecting it both into the tumor and around the periphery of the tumor.

In another embodiment, pharmaceutical compositions are administered systemically to the subject, for example, as in the case where the pharmaceutical compositions are administered intravenously, such as by injecting the composition into the subject's circulatory system.

In another illustrative embodiment, the pharmaceutical compositions are administered enterally, for example, to irrigate a tumor in the gastrointestinal tract.

The pharmaceutically acceptable excipients are selected, in accordance with the pharmaceutical form and method of administration desired, from the customary excipients, which are known to a person skilled in the art.

In the pharmaceutical compositions of the present invention, the nanoparticles according to the invention may be administered in a unit administration form, in a mixture with conventional pharmaceutical excipients, to animals and to human beings for the proxylaxis or treatment of cancer as defined above.

According to another advantageous embodiment, the nanoparticles according to the invention are in the form of a lyophilisate. Thus, ready-to-use stable lyophilized forms comprising said nanoparticles can be prepared and stored. Then, once the lyophilized powder is reconstituted with purified water, the pH and the osmolarity of the suspension are perfectly compatible with, for example, an intravenous injection.

By way of examples of pharmaceutical formulations compatible with the compositions according to the invention, mention may in particular be made of:
  intravenous injections;
  intravenous infusions.

When the nanoparticles are used as a dispersion in an aqueous solution, they may be combined with excipients such as sequestering or chelating agents, antioxidants, pH regulators and/or buffering agents.

In addition to the abovementioned compounds, the pharmaceutical compositions according to the invention may contain agents such as preservatives, wetting agents, solubilizing agents and colorants.

They may, however, contain other active agents of which it may be beneficial to take advantage from a therapeutic point of view, together with the effect of the platinum-based drug, in particular the platinum(II)-based drug.

By way of representation of these active materials that may be combined with the nanoparticles in accordance with the present invention, mention may in particular be made of other anticancer or cytostatic molecules or macromolecules (for example platinum salts distinct from platinum-based drug suitable for the present invention, 5-fluorouracile, folinic acid or salts thereof, anthracyclines, mitotic spindle poisons, topoisomerase inhibitors, kinase inhibitors or metalloprotease inhibitors), anti-inflammatories of corticoid type (for example dexamethasone) or noncorticoid type or else molecules with immunoadjuvant activity (for example antibodies with anticancer activity), molecules with analgesic activity, such as dextropropoxyphene, tramadol, nefopan, paracetamol, codeine, acetaminophen, non-steroidal anti-inflammatory drugs (NSAIDs), including aspirin, ibuprofen, indomethacin, unefenamic acid, oxicam derivatives, coxibs (Celecoxib®, Rofecoxib®, Valdecoxib®, Parecoxib®, for example) and sulfonanilides (Nimesulide® for example).

Mention may also be made of antioxidants, such as catechins, polyphenols, flavonols, flavonones, caffeine, ascorbic acid, citric acid, tartric acid, lecithins or natural or synthetic tocopherols.

The formulation of the platinum-based drug, in particular platinum(II)-based drug in the form of nanoparticles prevents any chemical condensation interaction between the other types of active agents and therefore allows them to be conditioned in the same galenical formula.

Dosage

There may be particular cases in which high or low dosages are appropriate; such dosages do not depart from the scope of the invention. According to usual practice, the dosage that is appropriate for each patient is determined by the doctor according to the mode of administration and the weight and response of the said patient.

For instance, the dosage administered—as single or multiple doses—to an individual will vary depending upon a variety of factors, including pharmacokinetic properties, patient conditions and characteristics (sex, age, body weight, health, size), extent of symptoms, concurrent treatments, frequency of treatment and the effect desired.

Monotherapy and Combination

For preventing and/or treating cancer, the nanoparticles according to the invention can be used in monotherapy. Monotherapy is advantageously recommended whether the patient or the subject in need thereof shows resistance towards certain other anti-cancer agents.

Alternatively, the nanoparticles according to the invention can be used in combination with at least one effective anticancer compounds with the same or with a different mechanism of action such as those defined above.

Accordingly, in another of its aspects, the nanoparticles according to the invention will be part of combination treatments comprising the administration of two or more anticancer compounds with related or unrelated mechanism of actions. Such a combination of the nanoparticles according to the invention and at least one other anti-cancer active principle(s) (different from the nanoparticles as defined in the present invention) can be comprised either in the same galenic formulation for example, such as the one disclosed previously, or in different galenic formulations.

According to an embodiment, when this combination is comprised in the same galenic formulation, the combination is preferably a fixed-dose combination in which the nanoparticles and at least one other anti-cancer active principle (distinct from these nanoparticles) can be formulated together for example in the same powder, vial.

According to another embodiment, when this combination is comprised in different galenic formulations, the administration of each of these active principles can be simultaneous or sequential.

In some embodiments, the nanoparticles in accordance with the invention can be administered prior to, after, or in combination with another anti-cancer agent, an anti-cancer therapy, or a surgery.

Method of Treatment

The present invention, according to another of its aspects, also provides a method of treating the pathologies indicated above, which comprises administering to a patient an effective dose of nanoparticles according to the invention, optionally in combination with other anti-cancer agents and/or with other active principles as defined above.

The examples which follow illustrate the present invention without, however, being limited thereto.

EXAMPLES

A. Materials and Methods

A.1. Chemicals

Dichloro(1,2-diaminocyclohexane)platinum(II) (DACHPt $Cl_2$, Mw=380.17 Da), silver nitrate $AgNO_3$ (Mw 169.97 Da), mannitol (Mw=182 Da) and N1 medium supplement 100× were purchased from Sigma Aldrich (Saint Quentin Fallavier, France). N1 medium supplement 100× contains 0.5 mg/ml recombinant human insulin, 0.5 mg/ml human transferrin (partially iron-saturated), 0.5 µg/ml sodium selenite, 1.6 mg/ml putrescine, and 0.73 µg/ml progesterone.

Poly-L-Arginine hydrochloride (Mw ranging from 5 kDa to 15 kDa) was purchased from Alamanda™ Polymers (Huntsville, USA).

Hyaluronic acid (HA, LMWHA (Mw 20 kDa)) was purchased from Lifecore Biomedical (Chaska, USA).

MTS cell titer 96® Aqueous One was provided by Promega (France).

Alexa Fluor 647 carboxylic acid, tris (triethylammonium) salt (0.8 mg/mi) (Invitrogen, Merelbeke, Belgium) was provided by Pr Katrien Remaut from Gent University, Belgium.

A.2: Characterization of Blank and DACHPt-Loaded Nanoparticles

A.2.1 Physicochemical Characterization of Nanoparticles

Particle size analysis and zeta potential measurements of tested nanoparticles were measured using a Malvern Zetasizer® apparatus DTS 1060 (Nano Series ZS, Malvern Instruments S.A., Worcestershire, UK) at 25° C., in triplicate, after a 1/60 dilution of nanoparticles dispersions with deionized water.

Morphological analyses were performed by transmission electron microscopy (TEM), using a JEM-1400 (JEOL, Tokyo, Japan) apparatus equipped with an Orius™ CCD Camera Controller (Gatan, Pleasanton Calif., USA).

The nanoparticles were fixed to Formvar® grids and dried for half-a-day and phosphotungstic acid 1% (w/v) was used as a negative contrast agent.

A.2.2 Entrapment Efficiency (EE) of DACHPt-Loaded Nanoparticles

The entrapment efficiency (EE) was determined using an indirect method. DACHPt-loaded sampled were put in an Amicon Ultra-filter centrifugation tube (Cut-off 30 kDa, Merck Millipore, Cork, Ireland) and centrifuged (7 000 g, 30 min, 20° C.). The concentration of the bottom solution was determined using and ICP-OES (Inductively Coupled Plasma Optical Emission Spectrometry) (ICP-OES ICAP 7200 duo Thermo Scientific).

A.2.3 Freeze-Drying of Blank and DACHPt-Loaded Nanoparticles

In order to lyophilize the nanosystems, blank and DACHPt-loaded nanoparticles were prepared dissolving HA and PArg into a mannitol 10% w/v solution. Mannitol 10% (w/w) was chosen as the cryoprotectant as it displayed the best performances in the conservation of physicochemical characteristics of the nanoparticles (data not shown). The freeze-drying process was performed using an ALPHA 1-4 LSC (CHRIST) freeze dryer equipped with an RZ6 Vacubrand pomp (Fisher Scientific, Illkirch, France). Size, Polydispersity, zeta potential and entrapment efficiency were evaluated after resuspension of the powder in water.

A.2.4 Single Particle Tracking of Fluorescent DACHPt-Loaded Nanoparticles in Serum and Distilled Water Fluorescence Single particle tracking (fSPT) was used to characterize the diffusion of nanoparticles in buffer and serum.

In this respect, fSPT makes use of an iXon ultra EMCCD camera (Andor Technology, Belfast, UK) and swept-field confocal (SFC) microscope (Nikon eclipse Ti, Japan) equipped with an MLC 400 B laser (Agilent technologies, California, USA) to obtain movies of single, fluorescently labeled particles. Analyzing these movies with in-house image processing software leads to a distribution of diffusion coefficients, which is converted into size distribution using the Stokes-Einstein equation taken into account the viscosity of the biofluids at which the experiment was performed. SPT is ideally suited to characterize the size of nanoparticles in biological fluids like human serum, ascites fluid, human plasma, and blood.

The main advantage of fSPT over the widely used sizing techniques such as Dynamic Light Scattering (DLS), is the ability to perform sizing measurements in undiluted biological fluids, without the influence of the proteins present in these fluids.

SPT measurements on F-PArg-HA nanoparticles in 90% vol. of biological fluids were performed as described below.

Firstly, the nanoformulations were diluted 15 times in distilled water. Then 5 µl of the prepared dilution was added to 45 µl of buffer or human serum (90% vol.) and incubated for 1 hour at 37° C. Then, 7 µl of sample was mounted on the microscope slide in the middle of secure-seal adhesive spacer (8 wells, 9 mm diameter, 0.12 mm deep, Invitrogen, Merelbeke, Belgium). The slide was covered by cover slip (24×50 mm) in order to avoid evaporation of the sample and allow for free diffusion entirely. Subsequently, the slide was placed on the swept field confocal microscope and movies were recorded focused at about 5 μm above the bottom of microscope slide. Videos were recorded at room temperature (22.5° C.) with the NIS Elements software (Nikon, Japan) driving the EMCCD camera and a swept-field confocal microscope equipped with a CFI Plan Apo VC 100× NA1.4 oil immersion objective lens (Nikon, Japan).

Analysis of the videos was performed using in-house developed software. Human serum was obtained from a healthy donor as described before.

A. Preparation of Nanoparticles of Blank, DACHPt-Loaded Nanoparticles and Fluorescent HA-PArg Nanoparticles Blank and DACHPt-loaded nanoparticles made of Hyaluronic acid (HA) and Polyarginine (PArg) were prepared using the ionotropic gelation method as explained below.

Example 1: DACHPt Preparation

DACHPtCl$_2$ (5 mM, 9.504 mg) was suspended in distilled water and mixed with silver nitrate (AgNO$_3$) (4.24 mg) ([AgNO$_3$]/[DACHPt]=1) to form the aqueous complex DACHPt. The solution was kept in the dark under magnetic stirring at 25° C. for 24 h. Silver chloride (AgCl) precipitates were found after reaction. The mixture was centrifuged at 2000 g for 20 min to eliminate the AgCl precipitates. Afterwards, the supernatant was purified by filtration using 0.22 μm filter in order to ensure sterility.

Example 2: Preparation of PArg Solution

PArg was prepared by modifying the PArg-Cl with an ion exchange resin (Amberlite® IRA 900 Cl). Briefly, 3 mL of NaOH (1M) were added to a column containing 1 ml of wet resin. After 30 minutes, the column was rinsed with purified water until the pH of the solution reached a neutral pH. Then, PArg-Cl solution (50 mg/me (1 ml) was put on the top of the column and PArg-OH was recovered at the bottom and then rinsed with purified water (2-3 ml) until the solution reached the desired concentration (12.5 mg/mL). The volume was measured in order to confirm the dilution up to 12 mg/ml.

Example 3: Preparation and Physical Characterization of Blank Nanoparticles

Blank nanoparticles, that is to say nanoparticles non-loaded with a platinum-based drug, were obtained by modifying the method already described by Oyarzun-Ampuero et al (*Eur J Pharm Biopharm Off J Arbeitsgemeinschaft Für Pharm Verfahrenstechnik eV.* 2011; 79(1):54-57).

Prior to their uses, the PArg-OH solution and the HA solution were filtered with a 0.22 μm filter to ensure sterility.

500 μl of PArg-OH solution (2.5 mg/ml) of example 2 and 500 μl of distilled water were mixed together in a vial. Then, 500 μL of HA solution (different concentrations ranging from 0.5 to 12 mg/ml) were added and the solution was left under magnetic stirring during 10 min at room temperature.

All the formulations were prepared dissolving the polymer in presence of mannitol 10% w/v.

Table 1 shows the screened [HA]/[PArg] mass ratios and the corresponding physicochemical properties that is to say size, polydispersity index (PDI) and zeta potential (ZP) of blank nanoparticles formulations with n being at least equal to 3 (that is to say triplicate or more):

TABLE 1

| [HA]/[Parg] ratio (w/w) | Size (nm) | PDI | ZP (mV) |
|---|---|---|---|
| 6/2.5 | 203.1 ± 7.8 | 0.198 | −39.9 ± 9.3 |
| 7/2.5 | 223.6 ± 36.6 | 0.181 | −32 ± 2.8 |
| 8/2.5 | 219.6 ± 9.8 | 0.156 | −34.6 ± 2.3 |
| 9/2.5 | 203.3 ± 3.3 | 0.160 | −37.2 ± 2.2 |
| 10/2.5 | 227.3 ± 20.4 | 0.199 | −40 ± 7.9 |
| 11.25/2.5 | 205.7 ± 5.7 | 0.163 | −32.8 ± 3.2 |

Example 4: Preparation and Physical Characterization of DACHPt-Loaded Nanoparticles According to the Invention. Impact of the HA/PArg Mass Ratio To obtain DACHPt-loaded nanoparticles, 500 μl of DACHPt solution obtained from example 1 were added to PArg-OH solution obtained from example 2 instead of water and the same process described for non-loaded nanoparticles in example 3 was followed. More particularly, DACHPt solution obtained from example 1 was mixed with PArg-OH solution obtained from example 2 and left under stirring for 10 min. The addition of HA to the DACHPt-PArg-OH solution led to the formation of loaded nanoparticles.

The pH and osmolality were checked for all the formulations prepared.

To isolate the system, 1 mL of nanoparticles suspension was transferred to Eppendorf tubes and centrifuged (16 000 g, 30 min, 25° C.) in 20 μL of a glycerol bed.

Supernatants were discarded, and the nanoparticles were resuspended in water using a pipette and vigorous vortexing.

To determine the contribution of polymers to the nano-systems and to customize the nanoparticles for the incorporation of positively charged hydrophilic molecule as DACHPt, several HA/PArg mass ratio were screened. All the formulations were prepared in presence of mannitol 10% w/v.

Table 2 shows the screened [HA]/[PArg] mass ratios and the corresponding physicochemical properties that is to say size, pH, polydispersity index (PDI) and zeta potential (ZP) of DACHPt-loaded nanoparticles formulations with n being at least equal to 3 (that is to say triplicate or more) and 660 μg DACHPt/mL of formulation.

TABLE 2

| [HA]/[Parg] ratio (w/w) | Size (nm) | PDI | ZP (mV) | pH |
|---|---|---|---|---|
| 0.5/2.5 | 104.8 ± 3 | 0.133 | +21.9 ± 3.2 | 5.13 |
| 4/2.5 | 130 ± 2.3 | 0.038 | −37.5 ± 1.5 | 5.71 |
| 7/2.5 | 153.3 ± 1.7 | 0.047 | −45.9 ± 1.7 | 5.66 |
| 9/2.5 | 176.5 ± 2.5 | 0.06 | −38 ± 1.3 | 5.55 |
| 10/2.5 | 159.6 ± 1.1 | 0.029 | −45.8 ± 0.6 | 5.74 |
| 11.25/2.5 | 161 ± 4 | 0.054 | −41.6 ± 3.8 | 5.76 |

It comes out from these results that DACHPt-loaded nanoparticles were smaller than the corresponding blank systems.

The charge ratio (negative charges on positive charges) goes up from 1.34 to 1.89 when the molar proportions are taken account of, as the platinum brings more positive charges to the formulation and therefore potentially increases the reticulation of the system.

Further, the polydispersity index is in an acceptable range (<0.2) for all the formulations tested indicating that the population obtained is quite homogeneous and monodispersed.

Furthermore, the zeta potential is negative and doesn't differ much from one ratio to another once the ratio is over 4/2.5.

To confirm the structure of the nanoparticles, Transmission Electron Microscopy (TEM) analysis was performed to study the morphological structure of DACHPt-loaded nanoparticles with a [HA]/[PArg] mass ratio being of 11.25/2.5. Nanoparticles were stained with phosphotungstic acid (1% w/v) as a contrast agent. The images obtained showed that the nanocarriers were spherical, not aggregated and well delimited. The size and polydispersity observed are in congruence with the results obtained with dynamic light scattering.

Example 5: Preparation of Fluorescent HA-PArg Nanoparticles

Alexa Fluor 647 carboxylic acid was employed as a means to label the PArg-HA nanoformulations.

In this respect, 80 µl of PArg-OH solution (2.5 mg/ml) and 120 µl of Alexa Fluor 647 carboxylic acid, tris (triethylammonium) salt (0.8 mg/ml) (Invitrogen, Merelbeke, Belgium) were mixed in a glass amber vial by magnetic stirrer. Then, 100 µl of HA solution (9 mg/ml) was added to the middle of vortex and the dispersion was kept under magnetic stirring for 10 minutes.

To isolate the nanoparticles, 300 µl of the nanocarrier dispersion was transferred to an Eppendorf microtube containing 20 µl of glycerol and centrifuged at 16000 g for 30 minutes at 25° C. Subsequently, the supernatant was discarded and pellet was resuspended in distilled water through vigorous vortexing. The fluorescently labeled nanoparticles were stored at 4° C. afterwards.

B. Impact of the Presence of PArg in the Formation of DACHPt-Loaded Nanoparticles HA solution (at a concentration ranging from of 9 and 11.25 mg/ml) with DACHPt solution were mixed in order to see if the presence or PArg was necessary to form nanoparticles.

No nanoparticles formation was observed with DLS (Dynamic Light Scattering), highlighting the importance of PArg and HA interaction to obtain stable nanosystems.

C. Entrapment Efficiency (EE) of DACHPt to Nanoparticles

A determination of the entrapment efficiency of DACHPt to different formulations (prepared at different HA/PArg ratio) after freeze-drying was performed.

The entrapment efficiency was evaluated using the ICP-OES (Inductively Coupled Plasma Optical Emission Spectrometry), as stated in the material and method section. The entrapment efficiency before freeze-drying was relevant as the formulation is intended and designed to be used after reconstitution. Moreover, the freeze-drying increases the EE significantly.

Table 3 shows the Entrapment efficiency and osmolarity of the reconstituted solution after freeze-drying depending on the HA/PArg ratio, with n being at least equal to 3 (that is to say triplicate or more).

TABLE 3

| [HA]/[Parg] ratio (w/w) | Entrapment efficiency (%) | Osmolarity |
|---|---|---|
| 3/2.5 (=1.2) | 46.2 ± 3.3 | NA |
| 4/2.5 (=1.6) | 54.3 ± 3 | 260 ± 14 |
| 7/2.5 (=2.8) | 66.5 ± 3.7 | 263 ± 2 |
| 9/2.5 (=3.6) | 68 ± 0.3 | 266 ± 9 |
| 10/2.5 (=4) | 72 ± 2.1 | 276 ± 16 |
| 11.25/2.5 (=4.5) | 70.1 ± 2.8 | 267 ± 14 |
| 12/2.5 (=4.8) | 69.6 ± 1.3 | 274 ± 5 |

It comes out from these results that the entrapment of DACHPt to nanoparticles, after freeze-drying, is particularly efficient when the [HA]/[Parg] weight ratio is higher than or equal to 2.

D. Stability of Blank and DACHPt-Loaded Nanoparticles

The stability of nanoparticles in terms of size and zeta potential was followed after freeze-drying which was carried out according to the method as described above.

As shown in table 4, size increases for all the nanoparticles tested, but this variation was not associated to a loss of stability of the system. All samples were kept at +4° C. for 1 to 3 months, in a dark in brown glass vial, as the DACHPt is sensitive to light. The vials were sealed using rubber caps and aluminum seals. The stability in size was assessed with DLS and remains stable at least 4 weeks after reconstitution. Moreover, the osmolarity observed after reconstitution is quite close to the one of human plasma (290 mmol/L) therefore suitable for IV (intravenous) injection (Table 3).

Table 4 shows physicochemical properties of DACHPt-loaded HA-PArg nanoparticles before and after freeze-drying at different mass ratios of [HA]/[PArg], with n being at least equal to 3 (that is to say triplicate or more).

TABLE 4

| [HA]/[Parg] ratio (w/w) | Size (nm) | | PDI | | ZP (mV) | |
|---|---|---|---|---|---|---|
| Freeze-drying | Before | After | Before | After | Before | After |
| 4/2.5 | 130 ± 2.3 | 244 ± 3.9 | 0.038 | 0.021 | −37.5 ± 1.5 | −41.9 ± 0.8 |
| 7/2.5 | 153.3 ± 1.7 | 234.5 ± 2.2 | 0.047 | 0.126 | −45.9 ± 1.7 | −46.2 ± 1.4 |
| 9/2.5 | 176.5 ± 2.5 | 241.7 ± 15 | 0.06 | 0.102 | −38 ± 1.3 | −44.1 ± 4.4 |
| 10/2.5 | 159.6 ± 1.1 | 240.9 ± 9.5 | 0.029 | 0.116 | −45.8 ± 0.6 | −41.2 ± 3.4 |
| 11.25/2.5 | 161 ± 4 | 237.5 ± 10.5 | 0.054 | 0.116 | −41.6 ± 3.8 | −46.8 ± 3.5 |
| 12/2.5 | 163 ± 3 | 235.6 ± 7.8 | 0.048 | 0.108 | −46.9 ± 6.2 | −40.4 ± 6.2 |

E. Single Particle Tracking (SPT) of Fluorescent DACHPT-Loaded Nanoparticles in Human Serum and Distilled Water It is proven that presence of proteins in biological fluids can scatter the light during DLS measurements, thereby interfering in evaluation of nanoparticles characteristics. Considering that DLS is a challenging technique for studying the physicochemical properties of nanoparticles in biological fluids, SPT has been proposed as a powerful method to measure the size of nanosystems in undiluted biofluids for instance human serum, blood and ascites.

FIG. 1 shows that when PArg-HA nanocarriers labeled with Alexa Fluor 647 were diluted in distilled water, an average size of 266 nm was obtained. Also, after incubation in 90% volume of human serum for 1 hour at 37° C., the nanoparticles showed a narrow size distribution with an average size of 275 nm.

The results demonstrate the colloidal stability of PArg-HA nanosystems under biological conditions which is pivotal for productive biomedical applications.

F. In Vitro Experiments

G.1 Cell Culture
Cell Lines

Human lung alveolar carcinoma A549 cells, provided by Prof. L. Migliore, University of Pisa, were grown in Ham's F12 medium supplemented with 10% Fetal Bovine Serum (FBS), 1 mM Gln, and antibiotics. Human colorectal adenocarcinoma HT-29 cells, provided by Prof. P. Petronini, University of Parma, were grown in DMEM High (glucose 4.5 g/l) supplemented with 10% FBS, 2 mM Gln and antibiotics. Cells were incubated at 37° C. at 5% CO2; after thawing, all cells were used for less than ten passages.

G.2 Viability Studies on B6KPC3, A549 and HT29 Cells: MTS Test
Cell Viability on B6KPC3, A549 and HT29

$3.5 \times 10^3$ B6KPC3 and A549 cells and $7.5 \times 10^3$ HT-29 cells were seeded into 96-well plates. After 24 h the medium was replaced with fresh, FBS-free growth medium, supplemented with 1% NEAA (Non Essential Amino Acids 100×, Gibco, Monza, Italy), sodium pyruvate 1 mM (Sigma-Aldrich, Milan, Italy), 1% N1 medium supplement (0.5 mg/mL recombinant human insulin, 0.5 mg/ml, human transferrin-partially iron-saturated-, 0.5 µg/mL sodium selenite, 1.6 mg/mL putrescine, and 0.73 µg/mL progesterone; Sigma-Aldrich), in the presence of increasing concentrations (0-200 µM) of commercially available Oxaliplatin (Oxaliplatin Hospira®, 5 mg/ml solution), DACHPt, blank and DACHPt-loaded HAPArg-NPs. After 24 h, cell viability was evaluated through MTS Cell Proliferation Colorimetric Assay Kit (Novus Biologicals, Abingdon, UK). Briefly, medium was removed, and 100 µL of MTS solution diluted 1:10 in serum-free medium were added in each well. In preliminary experiments the time of exposure to MTS (1 h for HT-29 and 3 h for A549 cells) was determined according to the metabolism of each cell type. Absorbance was measured at 492 nm with a microplate reader (EnSpire® Multimode Plate Reader, Perkin Elmer, Boston, Mass., USA).

Cell viability (CV) percentage was evaluated through the following formula:

CV (%)=(Absorbance(treated wells))/(Absorbance (control wells))×100 with Absorbance (control wells) considered the absorbance of untreated cells incubated in medium without drugs.

Figure 2:
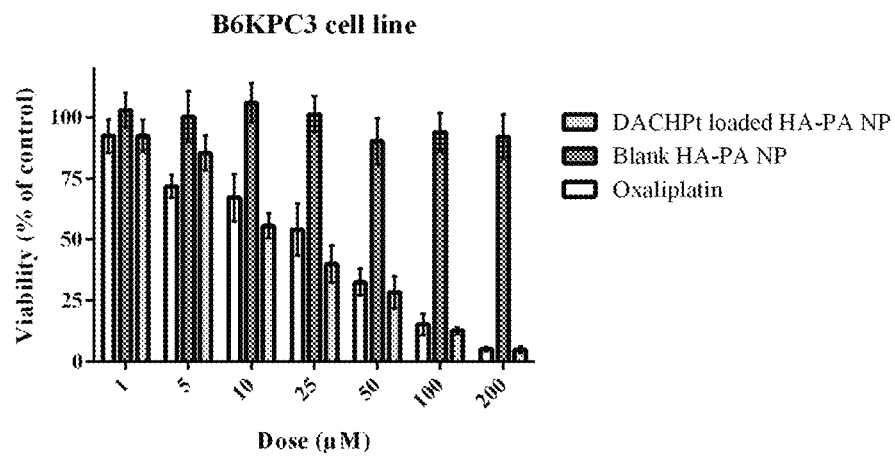
FIG. 2 illustrates the viability assessment performed on B6KPC3 (A), HT-29 (B) and A549 (C) cells after 24 h of incubation at 37° C. with increasing concentrations (0-200 µM) of oxaliplatin, blank NP and DACHPt-loaded NP for 24 hours (Mean±SD, n=6 (A) & n=3 (B and C)).
Figure 2:
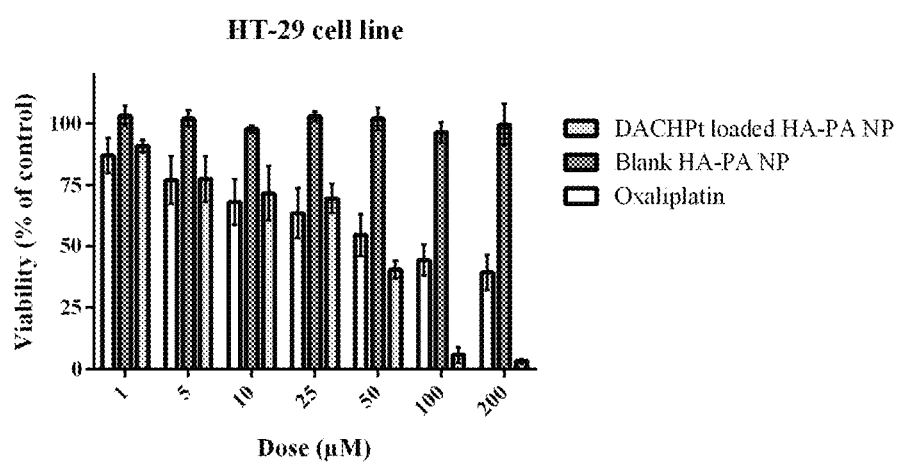
Figure 2:
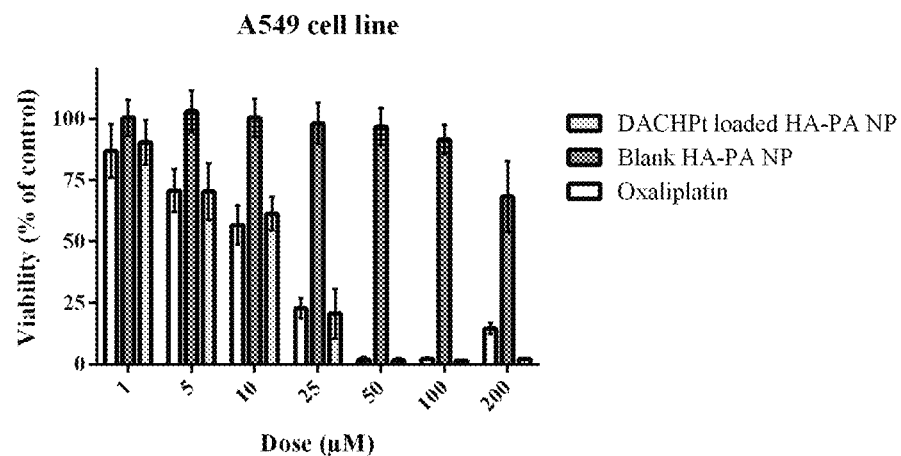

G.3 Results for Viability Studies on HT-29, A549 and B6KPC3 Cells: MTS Test B6KPC3 (FIG. 2A) HT-29 (FIG. 2B) and A549 cells (FIG. 2C) were incubated with increasing concentrations (0-200 µM) of Oxaliplatin (Oxaliplatin Hospira® 5 mg/ml), DACHPt, Blank nanoparticles and DACHPt-loaded NP for 48 h. Oxaliplatin, DACHPt, and Blank nanoparticles are thus used as controls. Viability was then evaluated with the MTS assay (see Material and Methods). Data were expressed as % of control (untreated cells). Data are means±SD of two experiments with 3 determinations each.

Dose response of B6KPC3 (see FIG. 2A), HT-29 (see FIG. 2B) and A549 (see FIG. 2C) cell viability to Oxaliplatin, DACHPt, Blank and DACHPt-loaded HAPArg-NPs. The results indicated that these cells were more sensitive to DACHPt than Oxaliplatin ($IC_{50}$ 39 µM of DACHPt versus 74 µM of Oxaliplatin for HT-29 cells. In the case of B6KPC3 cells, IC50 of DACHPt-loaded NP was 1.3 times lower (18 vs 23 µM) in comparison to the oxaliplatin solution, while NP toxicity was comparable to the oxaliplatin reference solution in A549 cell lines (IC50 11 and 12 µM, respectively). Blank NP did not interfere with cell viability at all the concentrations (Table 4 BIS)

Table 4 BIS—Calculated IC50 for B6KPC3, HT-29 and A549 cells lines after 24 h of incubation at 37° C. with increasing concentrations (0-200 µM) of oxaliplatin, DACHPt, Blank and DACHPt-loaded nanoparticles (Mean±SD, n=3).

TABLE 4

| | BIS | |
|---|---|---|
| Cell line | Oxaliplatin | DACHPt-loaded NP |
| HT-29 | 74 µM ± 2.9 | 39 µM ± 2.3 |
| B6KPC3 | 23 µM ± 1.0 | 18 µM ± 1.1 |
| A549 | 11 µM ± 2.2 | 12 µM ± 1.2 |

Example 6: Pharmacokinetics of DACHPt-Loaded Nanoparticles

A. Materials and Methods

Healthy mice (8 weeks female C57BL/6) were IV injected with 200 µl of DACHPt-loaded nanoparticles and oxaliplatin solution at a dose of 35.9 µg of platinum equivalent/mice.

At specific time points, 15, 30 min, 1, 1.5, 3, 5, 8 and 12 h post dose, 200 µl of blood was taken and separated from plasma. Pt content was detected using ICP/MS.

A compartmental PK analysis was done in Phoenix (Pharsight—a Certara™ L.P. software 1998-2014, Build 6.4.0.78) using WinNonlin 6.4, Connect 1.4. A first-order, two-compartment model with bolus administration, expressed in terms of CL and V was applied to fit the data, using $1/y_{hat}^2$ as weighting function. The model was either fitted using average data or individual data, and results were comparable in each of the cases.

Then, the model was used to simulate a multiple administration regimen. Eight cycles of 3.5 mg/kg of oxaliplatin solution or DACHPt-loaded nanoparticles were simulated using a twice weekly regimen (Marmiroli P. et al., *Susceptibility of different mouse strains to oxaliplatin peripheral neurotoxicity: Phenotypic and genotypic insights, PLoS One*). The average body weight was 25 g and the absolute dose 87.5 µg per mouse. The regimen schedule was: IV infusion (2 h) on days 1-4-8-11-15-18-22 and 25, or a total of 2 doses/week for 4 weeks.

B. Results

Figure 3B:
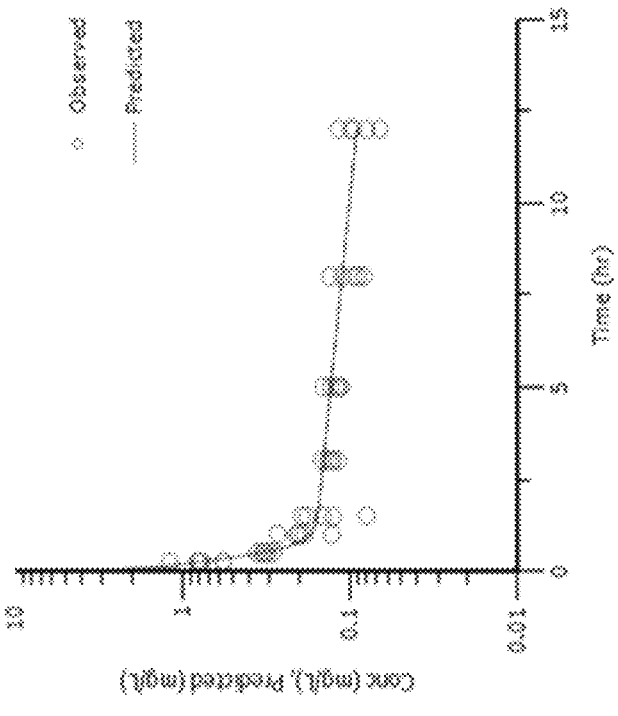
FIGS. 3A and 3B illustrate the plasma concentration-time curves of Pt derivatives after IV bolus injection of 35.9 µg DACHPt-loaded nanoparticles (A) or oxaliplatin solution (B) to mice. Circle symbols "○" represent the observed plasma concentrations in the individual mice. The line curve represents the best fit calculated from the data. In A, Abscisa: Time as expressed in hours. Ordinate, DACHPt concentration as expressed in mg/L. In B, Abscisa: Time as expressed in hours. Ordinate, oxaliplatin solution concentration as expressed in mg/L.
Figure 3A:
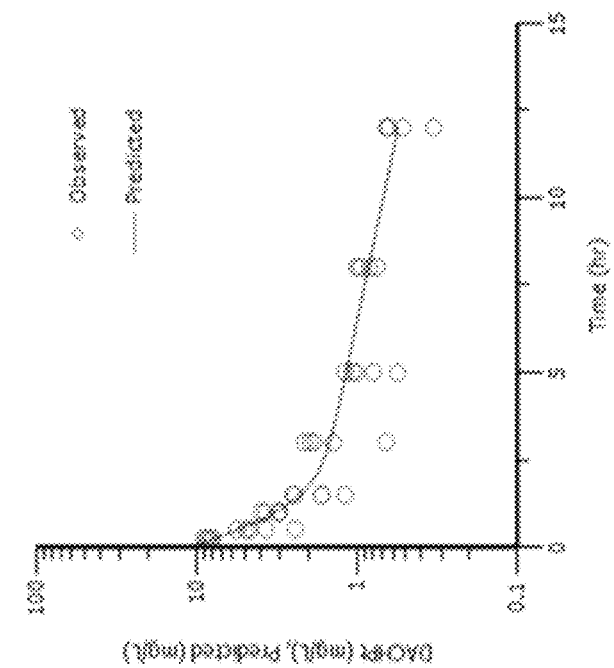

For some drugs, the plasma concentration-time curve following IV bolus injection displays a clear biphasic pattern. This biphasic pattern is the result of extensive distribution of platinum derivatives into different tissues, followed by their terminal elimination from the body. Based on the profile obtained (FIGS. 3A and 3B), the data were analyzed using a two-compartmental model. The Pt concentrations and DACHPt concentrations derived from DACHPt-loaded nanoparticles were evaluated and compared, and the results were equivalent. Finally, Pt concentrations derived from oxaliplatin solution and DACHPt concentrations derived from DACHPt-loaded nanoparticles were plotted as a function of time.

Parameters obtained from the fitted curves are displayed in Table 5 hereunder.

TABLE 5

Pharmacokinetic parameters following IV bolus injection of an equivalent dose of 35 μg Pt/mice of DACHPt-loaded nanoparticles or oxaliplatin solution.

| PARAMETER | UNITS | DACHPt loaded nanoparticles (mean ± SE) ESTIMATE | Oxaliplatin (mean ± SE) ESTIMATE |
|---|---|---|---|
| AUC | hr*mg/L | 23.8 ± 1.52 | 3.76 ± 0.52 |
| Alpha_HL | hr | 0.370 ± 0.075 | 0.135 ± 0.023 |
| Beta_HL | hr | 6.49 ± 1.08 | 13.6 ± 2.89 |
| K12 | 1/hr | 1.08 ± 0.26 | 4.14 ± 0.72 |
| K21 | 1/hr | 0.418 ± 0.088 | 0.398 ± 0.054 |
| Cmax | mg/L | 11.4 ± 1.82 | 2.48 ± 0.68 |
| AUMC | hr*hr*mg/L | 178 ± 37.8 | 65.1 ± 23.8 |
| Vss | L | 0.011 ± 0.001 | 0.165 ± 0.018 |
| Vc | L | 0.003 ± 0.0005 | 0.014 ± 0.004 |
| CL | L/hr | 0.002 ± 0.0001 | 0.010 ± 0.001 |
| Vp | L | 0.008 ± 0.001 | 0.15 ± 0.02 |
| Q | L/hr | 0.003 ± 0.0005 | 0.060 ± 0.008 |

From the PK results obtained, it can be observed that following the administration of DACHPt-nanoparticles, the AUC of the drug was of 24 hr*mg/L, six times higher than the value obtained following the administration of oxaliplatin solution, which was 3.76 hr*mg/L. The C max, defined as the maximal drug concentration detected in the blood at time 0 hr is 11.4 mg/L for nanoparticles and 2.48 mg/L for oxaliplatin solution, almost five times higher than the control drug.

The distribution and the elimination half-life indicated that when the drug is entrapped into nanoparticles, it is distributed (half-life alpha) slower (half-life alpha 0.370 hr for nanoparticles vs 0.135 hr for oxaliplatin solution).

However, the elimination rate (half-life beta) is more rapid in comparison with the oxaliplatin solution (half-life beta 6.49 hr for nanoparticles vs 13.6 hr for oxaliplatin solution).

The results showed that the Pt concentration in plasma starts at a lower level and initially decreases much more rapidly for the oxaliplatin solution as compared to the nanosystems. K12 (rate constant for distribution from central to peripheral compartment) is higher for oxaliplatin solution as compared to the one obtained with DACHPt nanoparticles (4.14 vs 1.08 hr$^{-1}$). While, K21 (rate constant for distribution from peripheral compartment to central compartment) is similar for oxaliplatin and DACHPt nanoparticles (0.398 and 0.418 lit$^t$).

Volumes of distribution of the central and peripheral compartment (Vc 0.003 and Vp 0.008 L for the nanoparticles vs Vc 0.014 and Vp 0.150 L for oxaliplatin solution) as well as the volume of distribution at steady state (Vss) were lower with the respect to the oxaliplatin solution (Vss 0.011 vs 0.165 L). Plasma clearance differed by a factor of six, being 0.002 and 0.010 L/h for nanoparticles and oxaliplatin solution respectively.

In order to study the maintenance of drug therapy, a repeated administration regimen was simulated. Repeated administration schedules are intended to minimize side effects while maintaining therapeutic drug concentrations in plasma and at the site of action. The number of doses, frequency and duration of cycles depend on the needs and the general state of the patients (Cisterna A et al. *Targeted nanoparticles for colorectal cancer, Nanomedicine (Lond).* 2016). In order to simulate an in vivo multiple administration regimen, it was decided to administer 8 cycles of 3.5 mg/kg of oxaliplatin solution or DACHPt-loaded nanoparticles (Marmiroli P. et al., *Susceptibility of different mouse strains to oxaliplatin peripheral neurotoxicity: Phenotypic and genotypic insights, PLoS One*).

Generally, factors affecting the average steady-state concentration are the rate of dose administration (in this case twice a week for 4 weeks) and plasma clearance. While the factors affecting the fluctuation of plasma concentration are frequency of drug administration and elimination half-life. In our dosing schedule, similar Pt doses with the same frequency were simulated. DACHPt nanoparticles and oxaliplatin solution have different plasma clearances, with the clearance of drug from the blood being lower for the nanoparticles than for the oxaliplatin solution.

However, the elimination half-life is distinct for both compounds being 13 hr for oxaliplatin solution and 6 hr for DACHPt nanoparticles.

From the simulation, it is evident that there was no accumulation of Pt and that steady-state was rapidly reached for the all the compounds plotted. Generally, in a repeated administration schedule, accumulation can occur when the drug is administered before the previous dose is completely eliminated. Then, the amount of drug in the body will progressively rise.

From our simulation results, it can be seen that the drug is always eliminated without accumulation. In the case of nanoparticles, the achievement of higher exposures during and immediately post dosing is evident. Then, the active compound concentration decreased rapidly for both oxaliplatin solution and DACHPt nanoparticles.

However, in the case of DACHPt, a higher exposure was maintained for at least two days, while in the case of oxaliplatin solution the amount of the drug detected in the blood is quite low even at the starting point.

These results are in line with the $C_{max}$ value obtained from the compartmental analysis. In fact, the maximal drug concentration detected in the blood at time 0 hr is five times higher for nanoparticles than for the control drug.

Based on this simulation, it is unequivocally shown that the administration of DACHPt nanoparticles can ensure a higher drug exposure over a prolonged time without drug accumulation.

In clinical studies, it was observed that, at the end of a 2-hr infusion of oxaliplatin, only 15% of the administered platinum was present in the systemic circulation. In line with the literature, the PK of platinum in human plasma ultrafiltrate after oxaliplatin administration is typically biphasic, characterized by a short initial distribution phase and a long terminal elimination phase. Moreover, platinum binds irreversibly to plasma proteins (predominantly serum albumin) and erythrocytes. Erythrocytes did not serve as a reservoir for platinum in the systemic circulation, and accumulation of platinum in blood cells is not considered to be of clinical relevance. (M. A. Graham, G. F. Lockwood, D. Greensdale, S. Brieza, M. Bayssas, E. Gamelin, *Clinical pharmacokinetics of oxaliplatin: a critical review*, Clin. Cancer Res. 6 (2000) 1205-1218.)

Taking together, the results from the compartmental analysis and the simulated multiple dose regimen, show that HA-PArg nanoparticles were able to associate the drug in an efficient manner, hampering rapid drug elimination due to DACHPt plasma protein binding. The C max and alpha half-life confirm this assumption. Moreover, the reduction in volume of distribution and clearance clearly indicate a more limited tissue distribution, no accumulation and a reduction of the efficiency of drug elimination when encapsulated.

From a deep analysis of the literature on pharmacokinetic evaluation of drug loaded Nanosystems we found that a significant effort has been spent on developing a long circulating nanoparticle formulation (*Preparation and biological properties of dichloro(1,2-diaminocyclohexane) platinum(II) (DACHPt)-loaded polymeric micelles, Journal of controlled release* 2005). However, prolonged circulation also means slow tissue distribution of the nanoparticles (including in the target tissue) and very slow drug release. In addition, in the case of oxaliplatin, if the drug is released into the blood as discussed earlier, it will bind to proteins or erythrocytes. Hence, a right balance between long circulating properties, and distribution and elimination rate is needed to avoid secondary effects (*Pharmacokinetics and Biodistribution of Nanoparticles, Molecular pharmaceutics* 2008).

The results here presented are associated with a high stability (high drug exposure), slower release and elimination of the nanoparticles as compared to the drug alone.

Example 7: Association Efficiency of DACHPt-Loaded Nanoparticles Prepared with Different PARg-OH/PARg-Cl Weight Ratio Protocol to Obtain PArgOH and PArgCl (Mixed Together)—HA Nanoparticles To study the influence of Cl ions coming from PArg Cl, nanoparticles containing different mass ratio or weight ratio of PArgOH and PArgCL were obtained.

Prior to their uses, the PArg-OH and PArg-Cl solution and the HA solution were filtered with a 0.22 µm filter to ensure sterility.

To obtain DACHPt-loaded nanoparticles, 500 µl of DACHPt solution obtained from example 1 above were added to a mixture of PArg-OH and PArg-Cl solution (mixed according the mass ratio indicated in table 6 below).

The addition of HA to the DACHPt-PArg-OH solution led to the formation of loaded nanoparticles.

The encapsulation efficiency (that is to say entrapment efficiency or association efficiency) was calculated as previous described. The encapsulation efficiency was evaluated following resuspension in water of freeze-dried nanoparticles.

Table 6 shows the impact of the PARg-OH/PARg-Cl weight ratio on the association efficiency in DACHPt-loaded nanoparticles.

TABLE 6

| Formulation | Amount of PARg-OH (% by weight) | Amount of PARg-Cl (% by weight) | Association efficiency (%) |
|---|---|---|---|
| HA-PARg nanoparticles | 100 | 0 | 72 ± 2 |
| | 75 | 25 | 58 ± 4 |
| | 50 | 50 | 50 ± 2 |
| | 25 | 75 | 56 ± 1 |
| | 0 | 100 | 47 ± 6 |

It comes out from these results that for the DACHPt-loaded nanoparticles, the greater the amount of PARg-OH, the more effective the encapsulation.

Example 8: Association Efficiency of Cisplatin-Loaded Nanoparticles

Protocol to Obtain Cisplatin Loaded HA-PArg Nanoparticles

To obtain Cisplatin loaded Ha-PArg nanoparticles, the same protocol described to obtain DACHPt nanoparticles was carried out. Cisplatin at the same concentration of DACHPt was mixed to Parg-OH solution and the same protocol described above was followed. The nanosystems were prepared in presence of Mannitol 10% w/v and freeze dried. Following resuspension the encapsulation efficiency was also evaluated according to the previous protocol.

Table 7 shows the association efficiency of cisplatin into HA/Parg (Chlorine free Nanosystems) before and after freeze-drying.

TABLE 7

| Platinum-based drug | Association efficiency (%) Before freeze-drying | Association efficiency (%) After freeze-drying |
|---|---|---|
| Cisplatin | 32 ± 2 | 74 ± 2 |

It comes out from these results that for the cisplatin-loaded nanoparticles, the association efficiency is greater after freeze-drying than before freeze-drying.

Example 9: In Vitro Studies to Assess Nanoparticles Activity

3D Cell Model: MCTS Formation and Treatment

Multi cellular tumor spheroids (MCTS) were formed according to a previous published method [Virgone-Carlotta A, Lemasson M, Mertani H C, et al. *In-depth phenotypic characterization of multicellular tumor spheroids: Effects of 5-Fluorouracil. PLOS ONE.* 2017; 12(11):e0188100. doi: 10.1371/journal.pone.0188100]. Briefly, MCTS were formed using HTC-116 cell line in Ultra Low Attachment (ULA) 96 wells Round-Bottom plate (Greiner bio-one) to avoid cell-substrate attachment. The cells were trypsinized and were counted using a Malassez grid in order to obtain 2,400 cells per milliliter. This concentration of cells (i.e., 480 cells per well in a volume of 200 µL) was chosen in order to obtain a single spheroid per well, with a spheroid diameter at the end of the experimentation not exceeding 500 µm. The plate was centrifuged for 5 minutes at 1,200 g at room temperature to initiate the formation of spheroids. The plate was placed in the incubator under agitation at 37° C. and 5% CO2 during the whole experiment. At the end of the first day after seeding, 100 µL of culture medium was added to ensure proper 3D growth. After two days after seeding, MCTS were treated with oxaliplatin aqueous solution, DACHPt-loaded nanoparticles (NP) at various drug concentrations: 5, 25 and 50 µM. The treatment was renewed during 3 days. Results are shown on FIGS. 4 to 6.

Blank NP were also used to assess nonspecific toxicity that could arise from the system. MCTS were monitored at day 0, 1, 2, 3, 4, and 7 day post treatment. Eight spheroids (n=8) were probed at each concentration (5, 25 and 50 µM). A ring of detaching cells appeared spontaneously after one day of treatment. The spheroids were transferred into new well plates to eliminate mechanically this uncohesive peripheral cell layer and to renew the drug and culture medium. Therefore, the reduction in volume monitored during treatment arose from a loss of viability as well as from a loss of cohesiveness.

Results are shown on tables 8-10 which illustrate the size reduction (%) of multicellular HT116 spheroids treated with blank, DACHPt-loaded nanoparticles (NP) and oxaliplatin (OXP) at 5, 25 and 50 µM respectively compared to the size of control spheroids at the same day.

TABLE 8

| | Drug concentration (µM) | Day 0 | Day 1 | Day 2 | Day 3 | Day 4 |
|---|---|---|---|---|---|---|
| Control | | | | | | |
| Loaded NP | 5 | −5.23 | 3.14 | 15.95 | 24.12 | 26.43 |
| Oxaliplatin | 5 | −1.21 | 4.52 | 15.86 | 24.88 | 28.73 |

TABLE 9

| | Drug concentration (µM) | Day 0 | Day 1 | Day 2 | Day 3 | Day 4 | Day 7 |
|---|---|---|---|---|---|---|---|
| Control | | | | | | | |
| Loaded NP | 25 | 2.44 | 17.64 | 31.89 | 45.05 | 51.09 | 56.46 |
| Oxaliplatin | 25 | 0.59 | 16.06 | 29.27 | 40.23 | 45.93 | 52.04 |

TABLE 10

| | Drug concentration (µM) | Day 0 | Day 1 | Day 2 | Day 3 | Day 4 | Day 7 |
|---|---|---|---|---|---|---|---|
| Control | | | | | | | |
| Blank NP | | 0.92 | 4.38 | 7.11 | 8.28 | 9.45 | |
| Loaded NP | 50 | 2.16 | 20.31 | 42.24 | 53.28 | 70.44 | 81.05 |
| Oxaliplatin | 50 | 0.62 | 16.78 | 32.53 | 44.17 | 48.93 | 71.67 |

Phase Contrast Follow Up of MCTS Volume

Photographs of MCTS were taken with an inverted microscope (Leica DMIRB) in phase contrast inside the 96-well plates at day 0, 1, 2, 3, 4, 7 time points after oxaliplatin exposure. We performed edge detection using a sobel threshold for each spheroid using the Image J software. The resulting binary images were fitted to an ellipse of major (LM) and minor (Lm) axes using the ImageJ "Analyse Particles" plugins. From this, a mean diameter was calculated, D=(LM+Lm)/2. The volume V was then determined assuming that the spheroids are spherical $V=\pi D^3/6$. Results are shown on FIG. 7.

Figure 4:
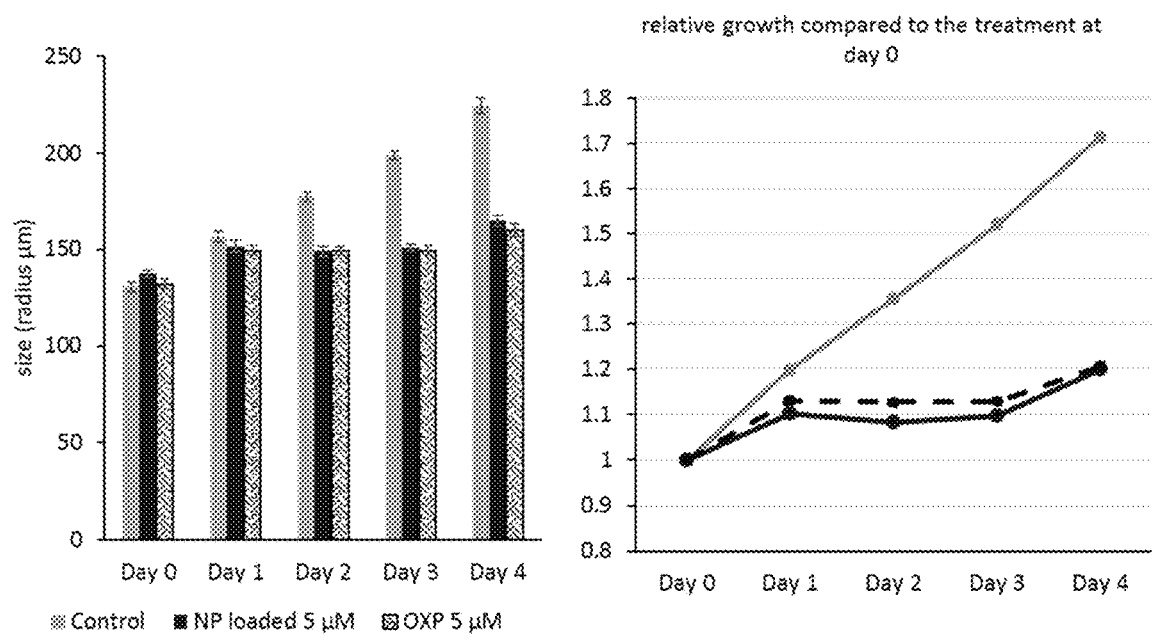
FIG. 4 illustrates the normalized volume of multicellular HT116 spheroids after treatment with DACHPt-loaded NP and oxaliplatin at 5 µM.
Figure 5:
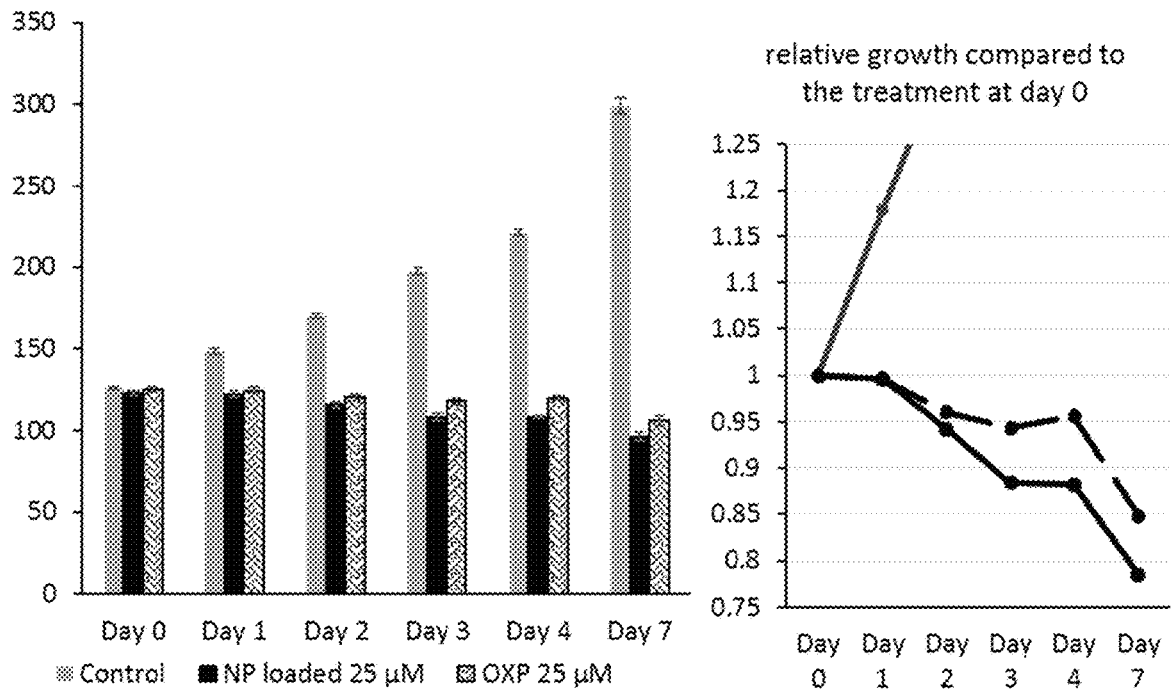
FIG. 5 illustrates the normalized volume of multicellular HT116 spheroids after treatment with DACHPt-loaded NP and oxaliplatin at 25 µM.
Figure 6:
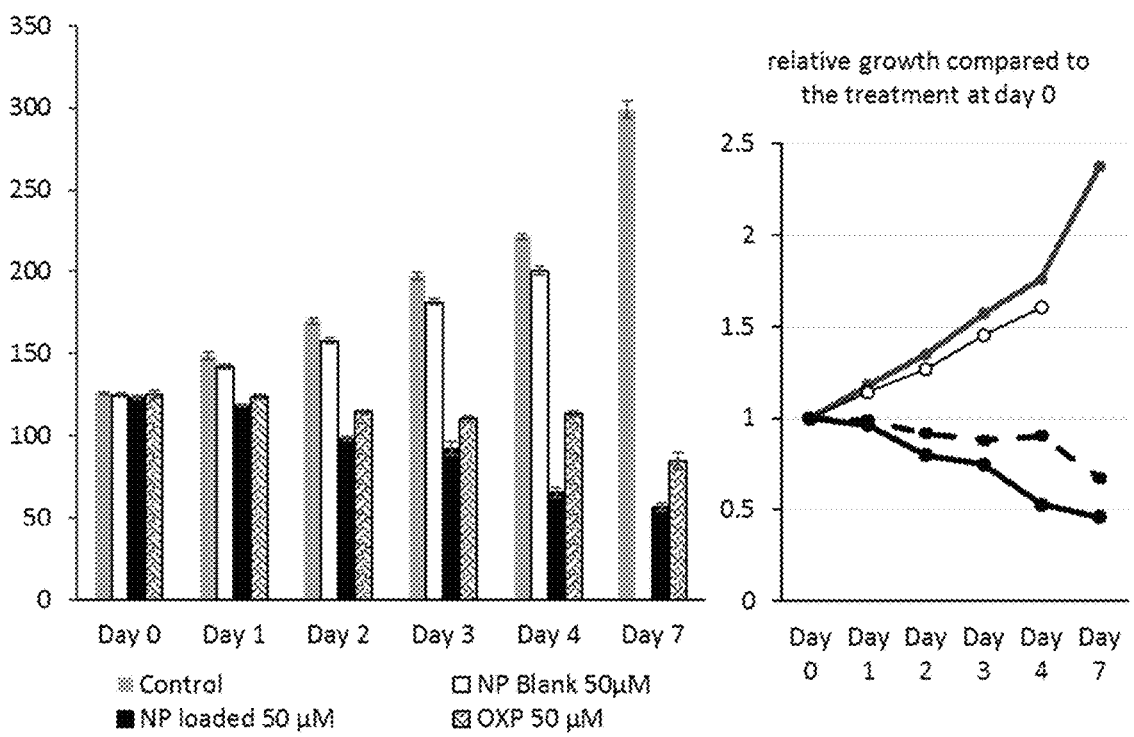
FIG. 6 illustrates the normalized volume of multicellular HT116 spheroids after treatment with blank, DACHPt-loaded NP and oxaliplatin at 50 µM.

Results:

To establish the impact on tumor viability of nanoparticles on a more lifelike in vitro culture system, the dose response of oxaliplatin solution in comparison with the DACHPt-loaded NP during 3 days of treatment on a MultiCellular Tumor Spheroids (MCTS) derived from the HCT-116 cell line has been tested. The volume of MCTS was evaluated from phase contrast microscopy images as a readout of cytotoxic effect. The data reported in FIGS. 4-6 represent normalized MCTS volume for different treatments with respect to the control volume (MCTS not treated). Three different drug concentrations were tested: 5, 25 and 50 µM.

As showed in FIGS. 4-6, DACHPt-loaded NP were able to reduce the volume of the spheroids after 2 days of treatment even at drug doses of 5 µM. The cytotoxic effect was more pronounced at higher doses (25 and 50 µM). After 7 days of observation for 25 and 50 µM drug concentration the reduction in tumor volume obtained using DACHPt-NP was more pronounced as compared to the oxaliplatin solution (FIGS. 5 and 6), suggesting a superiority in activity of the encapsulated drug as compared to oxaliplatin solution. Empty nanoparticles did not affect MCTS size.

Figure 7:
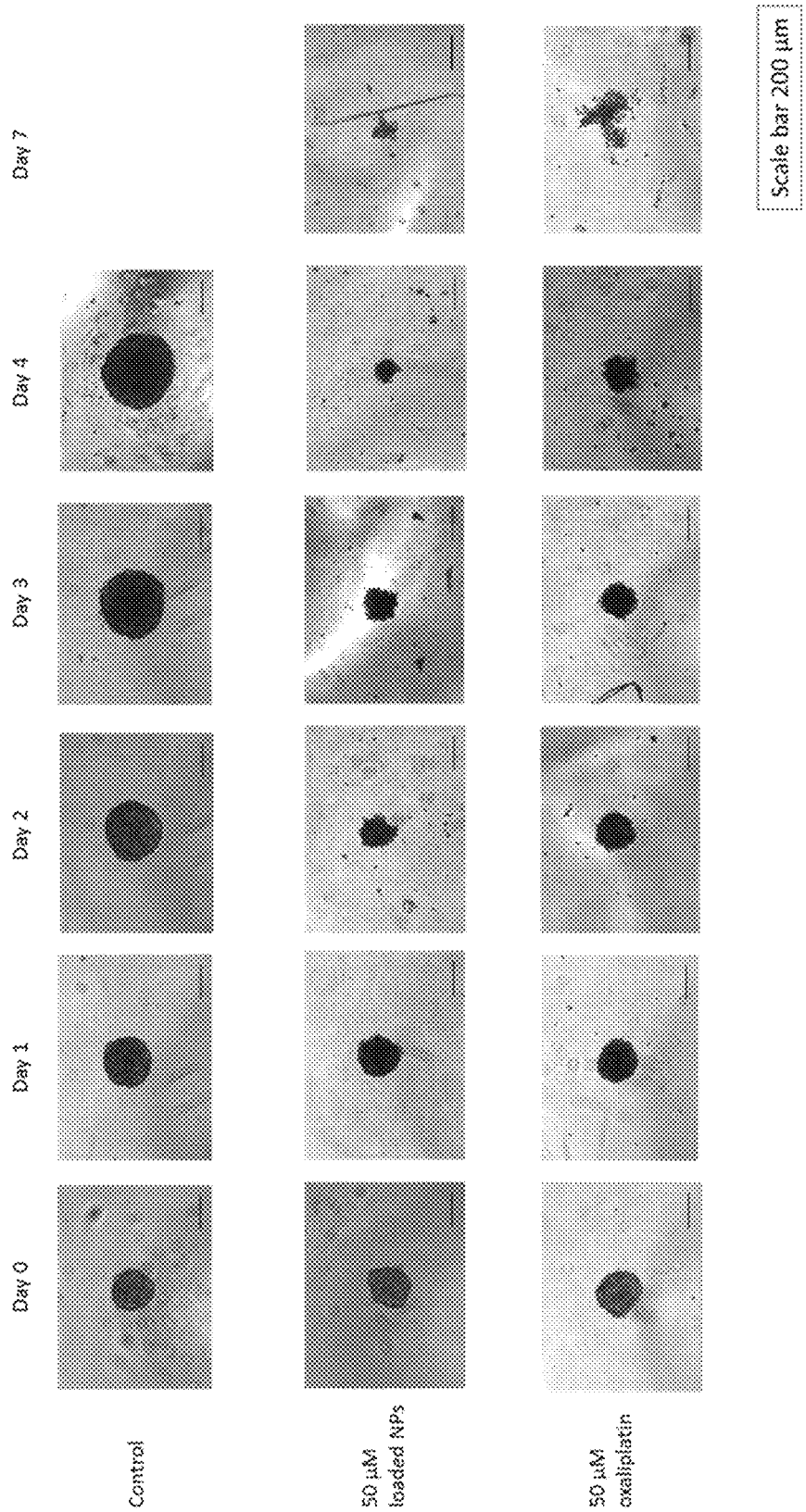
FIG. 7 are photographs of untreated multicellular HT116 spheroids and treated spheroids with DACHPt-loaded NP and oxaliplatin solution at 50 µM taken at day 0, 1, 2, 3, 4 and 7.

Photographs of treated MCTS were taken to show the evolution of the spheroids. In FIG. 7, untreated spheroids were compared with the MCTS treated with oxaliplatin and DACHPt-loaded NP at the highest concentration (50 µM). It can be noticed that treatment with DACHPt-NP induced a collapse of the spheroid, while in the case of oxaliplatin few cells are still present and formed aggregates.

The invention claimed is:

1. Nanoparticles useful as drug delivery system, said nanoparticles being formed from at least:
   (a) platinum-based drug,
   (b) poly-L-arginine, and
   (c) hyaluronic acid,
   wherein the platinum-based drug, poly-L-arginine, and hyaluronic acid are non-covalently coupled to one another, and
   wherein the platinum-based drug is a platinum complex selected from platinum complex (II), platinum complex (IV) and mixtures thereof.

2. The nanoparticles according to claim 1, wherein said poly-L-arginine of (b) is selected from poly-L-arginine hydroxide, poly-L-arginine hydrochloride and a mixture of poly-L-arginine hydroxide and of poly-L-arginine hydrochloride.

3. The nanoparticles according to claim 1, wherein the platinum-based drug is a platinum(II)-based drug which is chosen among di-aqua(1,2-diaminocyclohexane)platinum (II), oxaliplatin, carboplatin, nedaplatin, lobaplatin, heptaplatin, cis-diamminediaquaplatinum(II), di-aqua(1,2-diaminomethyl)cyclobutane)platinum(II), di-aqua(4,5-diaminomethyl-2-isopropyl-1,3-dioxolane)platinum(II) and mixtures thereof.

4. The nanoparticles according to claim 1, wherein said platinum-based drug of (a) is present under a form free from chlorine atom and said poly-L-arginine of (b) is poly-L-arginine hydroxide.

5. The nanoparticles according to claim 1, wherein said platinum-based drug of (a) contains chlorine atom(s) and said poly-L-arginine of (b) is poly-L-arginine hydrochloride.

6. The nanoparticles according to claim 1, wherein the hyaluronic acid and the poly-L-arginine are in a weight ratio of [hyaluronic acid]/[poly-L-arginine] that is higher than 0.5/2.5.

7. The nanoparticles according to claim 1, wherein the platinum-based drug, hyaluronic acid, and the poly-L-arginine are in a weight ratio of [platinum-based drug]/[hyaluronic acid]+[poly-L-arginine] ranging from 0.01 to 1.00.

8. A method for preparing nanoparticles according to claim 1, said method comprising at least the steps of:
   (i) providing a platinum-based drug under the form of an aqueous complex free from chlorine atom,
   (ii) providing an aqueous solution of poly-L-arginine free from chloride ion,
   (iii) mixing said platinum-based drug under the form of an aqueous complex of (i) and said aqueous solution of (ii)
   (iv) adding hyaluronic acid to the mixture obtained at step (iii) in conditions suitable for forming the nanoparticles, and optionally
   (v) recovering the nanoparticles obtained at step (iv).

9. The method according to claim 8, wherein the aqueous complex form is chosen among diaminediaquaplatinum(II), di-aqua(1,2-diaminocyclohexane)platinum(II) (DACHPt), di-aqua(1,2-diaminomethyl)cyclobutane)platinum(II), di-aqua(4,5-diaminomethyl-2-isopropyl-1,3-dioxolane)platinum(II), and their mixtures.

10. The method according to claim 8, wherein the poly-L-Arginine free from chloride ion (ii) is the poly-L-Arginine hydroxide.

11. Nanoparticles obtainable by the method according to claim 8.

12. A pharmaceutical composition comprising at least one nanoparticle as defined in claim 1 and at least one pharmaceutically acceptable excipient.

13. Nanoparticles as defined in claim 1 for use in the prevention/or treatment of cancer.

14. The nanoparticles for use according to claim 13, wherein the cancer is chosen among pancreatic cancer, colorectal cancer, lung cancer, small and non-small cell lung cancer, ovarian cancer, testicular cancer, breast cancer, brain cancer, sarcomas, lymphomas, head and neck cancer, metastatic colorectal cancer, gastric cancer, ovarian cancer, esophageal cancer, bladder cancer, cervix cancer, leukemia, prostate cancer, liver cancer, colon cancer, renal cancer, skin cancer, bone cancer, uterine cancer, lymphatic cancer, stomach cancer, and intestinal cancer.

15. A pharmaceutical composition comprising at least one nanoparticle as defined in claim 11 and at least one pharmaceutically acceptable excipient.

16. Nanoparticles as defined in claim 11 for use in the prevention/or treatment of cancer.

17. The nanoparticles for use according to claim 16, wherein the cancer is chosen among pancreatic cancer, colorectal cancer, lung cancer, small and non-small cell lung cancer, ovarian cancer, testicular cancer, breast cancer, brain cancer, sarcomas, lymphomas, head and neck cancer, metastatic colorectal cancer, gastric cancer, ovarian cancer, esophageal cancer, bladder cancer, cervix cancer, leukemia, prostate cancer, liver cancer, colon cancer, renal cancer, skin cancer, bone cancer, uterine cancer, lymphatic cancer, stomach cancer, and intestinal cancer.

18. The nanoparticles according to claim 4, wherein said platinum-based drug of (a) is di-aqua(1,2-diaminocyclohexane)platinum (II).

19. The nanoparticles for use according to claim 14, wherein the cancer chosen among pancreatic cancer is pancreatic ductal adenocarcinoma (PDAC).

20. The nanoparticles for use according to claim 14, wherein the leukemia is a chronic myeloid leukemia.

21. The nanoparticles for use according to claim 17, wherein the cancer chosen among pancreatic cancer is pancreatic ductal adenocarcinoma (PDAC).

22. The nanoparticles for use according to claim 17, wherein the leukemia is a chronic myeloid leukemia.

23. Nanoparticles useful as drug delivery system, said nanoparticles being formed from at least:
   (a) platinum-based drug in a form free from chlorine atoms,
   (b) poly-L-arginine hydroxide, and
   (c) hyaluronic acid,
   wherein the platinum-based drug is a platinum complex selected from platinum complex (II), platinum complex (IV) and mixtures thereof.

24. Nanoparticles useful as drug delivery system, said nanoparticles being formed from at least:
   (a) platinum-based drug,
   (b) poly-L-arginine, and
   (c) hyaluronic acid,
   wherein the platinum-based drug is a platinum complex selected from platinum complex (II), platinum complex (IV) and mixtures thereof, and
   wherein the hyaluronic acid and the poly-L-arginine are in a weight ratio of [hyaluronic acid]/[poly-L-arginine] that is higher than 0.5/2.5.

25. Nanoparticles useful as drug delivery system, said nanoparticles being formed from at least:
   (a) platinum-based drug,
   (b) poly-L-arginine, and
   (c) hyaluronic acid,
   wherein the platinum-based drug is a platinum complex selected from platinum complex (II), platinum complex (IV) and mixtures thereof, and
   wherein the platinum-based drug, hyaluronic acid, and the poly-L-arginine are in a weight ratio of [platinum-based drug]/[hyaluronic acid]+[poly-L-arginine] ranging from 0.01 to 1.00.

* * * * *